US006291741B1

(12) United States Patent
Paul et al.

(10) Patent No.: US 6,291,741 B1
(45) Date of Patent: Sep. 18, 2001

(54) METHOD FOR THE PRODUCTION OF MODIFIED PLANTS

(75) Inventors: Wyatt Paul, Cambridge; Roderick John Scott, Leicestershire, both of (GB); Andreas Betzner, Page; Eric Huttner, Aranda, both of (AU); Phillipe Lenee, New Caledonia; Pascual Perez, Chamonat, both of (FR)

(73) Assignees: Gene Shears Pty. Limited, Neutral Bay (AT); Nickerson Biocem Limited, Cambridge (GB)

( * ) Notice: Subject to any disclaimer, the term of this patent is extended or adjusted under 35 U.S.C. 154(b) by 0 days.

(21) Appl. No.: 08/682,767

(22) PCT Filed: Jan. 31, 1995

(86) PCT No.: PCT/GB95/00188

§ 371 Date: Jan. 9, 1997

§ 102(e) Date: Jan. 9, 1997

(87) PCT Pub. No.: WO95/20668

PCT Pub. Date: Aug. 3, 1995

(30) Foreign Application Priority Data

Jan. 31, 1994 (GB) .................................................. 9401780

(51) Int. Cl.⁷ .............................. C12N 15/82; A01H 1/02; A01H 5/00; A01H 5/10
(52) U.S. Cl. ......................... 800/274; 800/286; 800/287; 800/288; 800/303; 435/69.1; 435/199; 435/468; 536/24.5
(58) Field of Search ................................. 435/69.1, 172.3, 435/199, 172.1, 468; 536/24.1, 24.5; 800/205, 274, 285, 288, 286, 287, 298, 303; 47/58, DIG. 1

(56) References Cited

U.S. PATENT DOCUMENTS

| | | | |
|---|---|---|---|
| 4,990,607 | 2/1991 | Katagiri et al. | 435/69.1 |
| 5,750,867 | * 5/1998 | Williams et al. | 800/205 |

FOREIGN PATENT DOCUMENTS

| | | |
|---|---|---|
| 636717 | 5/1993 | (AU) . |
| 0412006 | 2/1991 | (EP) . |
| 0412911 | 2/1991 | (EP) . |
| 0425004 | 5/1991 | (EP) . |
| 0573767 | 12/1993 | (EP) . |
| 0589841 | 3/1994 | (EP) . |
| 9109957 | 7/1991 | (WO) . |
| 9113994 | 9/1991 | (WO) . |
| 9201799 | 2/1992 | (WO) . |
| 9419477 | 9/1994 | (WO) . |
| 9429465 | 12/1994 | (WO) . |

OTHER PUBLICATIONS

Mascarenhas, J. pp. 99–105 In: Mol. Basis Plant Dev., Goldberg, R., ed., Alan R. Liss, Inc. New York, 1989.*
Steinecke et al. EMBO J 11(4): 1525–1530, 1992.*
Edington et al. pp. 209–221 In: Gene Regulation: Biol. Antisense RNA+DNA, Erickson et al., eds., Raven Press: NY, 1992.*
Wegener et al. Mol. Gen. Genet. 245: 465–470, 1994.*
Steinecke et al. Gene 149: 47–54, 1994.*
Perriman et al. Proc. Natl. Acad. Sci. USA 92: 6175–6179, Jun. 1995.*
Atkins et al. J. Gen. Virol. 76: 1781–1796, 1995.*
Nakamura et al. Ann. Phytopathol. Soc. Jpn. 61: 53–55, 1995.*
Borovkov et al. J. Plant Physiol. 147: 644–652, 1996.*
de Feyter et al. Mol. Gen. Genet. 250: 329–338, 1996.*
McIntyre et al. Transgenic Research 5: 263–270, 1996.*
Yang et al. Proc. Natl. Acad. Sci. USA 94: 4861–4865, May 1997.*
Merlo et al. Plant Cell 10: 1603–1621, Oct. 1998.*
Evans et al. Biochem. Soc. Trans. 20: 3445, 1992.*
Mazzolini et al. Plant Mol. Biol. 20: 715–731, 1992.*
Turgut et al. Plant Mol. Biol. 24: 97–104, 1994.*
Lassner, M.W. et al., (1991). Targeting of T7 RNA polymerase to tobacco nuclei mediated by an SV40 nuclear location signal. Plant Molecular Biology, 17: 229–234.
Lloyd, A.M. et al., (1992). Arabidopsis and Nicotiana anthocyanin production activated by maize regulators R and Cl. Science 258: 1773–5.
Oeda, K. et al., (1991). A tobacco bZip transcription activator (TAF–1) binds to a G–box–like motif conserved in plant genes. The EMBO Journal, 10: 1793–1802.
Swinburne, J. et al., (1992). Elevated levels of activator transposase mRNA are associated with high frequencies of dissociation excision in Arabidopsis. The Plant Cell, 4: 583–595.

* cited by examiner

*Primary Examiner*—David T. Fox
(74) *Attorney, Agent, or Firm*—John P. White; Cooper & Dunham LLP

(57) ABSTRACT

Methods for the production of modified plants are provided. In these methods a first line and a second line are crossed to produce a plant having a phenotypic trait, wherein neither the first or second lines possess the phenotypic trait, and wherein at least one of the parent lines is transgenic. Plants produced by the methods of the invention are also described.

20 Claims, 9 Drawing Sheets

```
  1    .ATTCTGTTCTTGGTTTACTTAATCTTCTTTCTAGTTAAGTATATTCTTG  49
        || |    |||||||||   |   |    | |||   |   |||
  1    AATGGAATGGACAGTTTACTGTCTTAGTCTAAAAATGAACCTTTCTCTAT  50

50    TTGCTCATCACCAAAGCTTGTGATGGAGGCTCTCTTCTTGAGTTCTTCTT  99
       ||  |  |    |  ||  ||||||||||| |||||||||||||||||||
 51    TTCTTATT..TCTTAGTTTGTGATGGAAGCTCTCTTCTTGAGTTCTTCTT  98

100    CTTCCTCCATTGTAGGGTCAAACAAGCTTACTAGGTTACACAACCATTGT  149
       |  |||||||||  |   ||||  ||||||| |  || |||||| ||| ||
 99    CCTCCTCCATTGCTGCTTCAATCAAGCTTTCAAGATTACACGACCGTCGT  148

150    GTCTGGTCTACAGTGATTAGAGATAAGAAAAGGTTCGGTCCCACTTGGTG  199
       | ||||| || || | || ||  |||||||| | || ||||| |||||
149    GACTGGTGCACTTTGTTAAGGGACAAGAAAAGGGTAGGACCCACCTGGTG  198

200    CCGTGTAGGTGGTGGTGGTGATGGTGGGAGAAACAGTAACGCAGAGAGTC  249
       ||| |||||||||||||| |  || |||||||||| ||  |||||||| |
199    CCGCGTAGGTGGTGGTGGCGGTGATGGGAGAAACATCAAACCAGAGAGGC  248

250    CTATTCGGGTTTCTTCGCTTTTGAAAGACAGAGGTCAGGTACTGATTAGG  299
       ||| | |||| || || |||||||||||||||||||| ||| ||||||||
249    CTATTAGGGTCTCATCGCTTTTGAAAGACAGAGGTCAAGTATTGATTAGG  298

300    GAACAGAGTTCGCCGGCTATGGATGCTGAGACATTGGTTCTGTCTCCAAA  349
       |||||||||||||| |||||||| ||||||||||||||||||||| || ||
299    GAACAGAGTTCGCCTGCTATGGACGCTGAGACATTGGTTCTGTCACCTAA  348

350    CGGGAATGGGAGAACCATTGAGATCAATGGAGTAAAGACTTTGATGCCTT  399
        | ||||||  |  ||||||||||| |||||||  ||| |||||||||||
349    TGTGAATGGTACAGCCATTGAGATGAATGGAGTGAAAACTCTGATGCCTT  398

400    TTAGTGGCGCTTCTATGGTGGGGATGAAAGAAGGACTTGGCATAATCAGT  449
       |  |   |||  ||||||||||||| ||  |||||||||||| |  |||
399    TCAATGGTGCTGATATGGTGGGGATCAAACAAGGACTTGGCATCGTTAGT  448

450    TTCCTCCAAGGGAAGAAGTTTCTAATCACTGGCTCGACCGGTTTCTTAGC  499
       |  || |||||||||| ||||||||||||||||| || ||  ||||||||
449    TATCTACAAGGGAAGACGTTTCTAATCACTGGCTCCACTGGCTTCTTAGC  498

500    TAAAGTACTGATTGAGAAAGTCTTGAGAATGGCTCCTGATGTCAGCAAGA  549
       |||||||||||||||||| |||||||||||||||||||||||  | |||
499    TAAAGTACTGATTGAGAAGGTCTTGAGAATGGCTCCTGATGTTGGGAAAA  548

550    TATATCTCTTGATTAAAGCCAAAAGCAAAGAAGCTGCGATCGAGCGGCTA  599
       ||||||||||||||||||| ||||  ||||||||| |||||| ||||| ||
549    TATATCTCTTGATTAAAGCTAAAAACAAAGAAGCAGCGATCCAGCGGTTA  598

600    AAGAACGAGGTGTTAGATGCAGAGCTTTTAATACTCTAAAAGAGACTCA  649
       ||||||||||||||||||||||||||||| | ||||| ||||||||||
599    AAGAACGAGGTGTTAGATGCAGAGCTTTTAAAAATCTAAGAGAGACTCA  648

650    TGGAGCATCTTACATGTCTTTCATGTTAACTAAACTCATCCCTGTGACCG  699
       |||||||||||  ||||||||||||||| || || |||||||||||| |
649    TGGAGCATCTTTCATGTCTTTCATGTTAGACAAGCTTGTCCCTGTGACAG  698
```

FIG. 5.II

```
 700 GAAACATTTGCGATTCAAACATTGGGTTGCAAGCAGATTCAGCTGAAGAG  749
     ||||||||||||||||||||||||||||||||||| ||||||||| || |||
 699 GAAACATTTGCGATTCAAACATTGGGTTGCAAACAGATTCAGCAGAGGAG  748

750 ATTGCGAAAGAAGTTGATGTTATAATCAATTCTGCTGCTAATACAACCTT  799
     ||||| ||||||||||||||| || ||||| || ||||| ||||||||||
 749 ATTGCAAAAGAAGTTGATGTGATTATCAACTCAGCTGCCAATACAACCTT  798

800 CAATGAAAGATACGATGTTGCTCTGGACATCAACACAAGAGGGCCCGGTA  849
     |||||||||||| ||||||||||| |||||| ||||| |||||| ||||
 799 CAATGAAAGATATGATGTTGCTTTGGACATAAACACACGAGGGCCTGGTA  848

850 ATCTCATGGGATTCGCCAAGAAGTGCAAGAAACTCAAACTGTTCTTGCAA  899
     |||||||||||||||||||||||||||||||||||| || |||||||||
 849 ATCTCATGGGATTCGCCAAGAAGTGCAAGAAACTCAAGCTTTTCTTGCAA  898

900 GTATCCACAGCTTATGTGAATGGACAAAGACAAGGAAGGATCATGGAGAA  949
     ||||| |||||||||||||| |||||||||||||||||||||||||||||
 899 GTATCTACAGCTTATGTGAACGGACAAAGACAAGGAAGGATCATGGAGAA  948

950 GCCATTTTCTATGGGAGATTGTATAGCAACAGAGAACTTCCTCGAAGGAA  999
     ||| || || |||||||||||||||| |||||||||||| |||||| |
 949 GCCCTTCTCGATGGGAGATTGTATAGCTACAGAGAACTTCATGGAAGGTA  998

1000 ACAGAAAGCATTAGATGTTGATAGAGAGATGAAGTTAGCTCTTGAAGCT  1049
     |||| |||||||||||| | |||| ||||||||||| ||||||||| |||
 999 ACAGGAAAGCATTAGATATCGATAAAGAGATGAAGCTAGCTCTTGATGCT 1048

1050 GCTAGAAAAGGGACTCAAAATCAAGATGAGGCACAGAAGATGAAGGATCT  1099
     || | |||||||||||||| |||||||||||| |||||||||||||||||
1049 GCAAGAAAAGGGACTCAAGATCAAGATGAGGCGCAGAAGATGAAGGATCT  1098

1100 CGGTCTAGAGCGGGCAAGATCATATGGATGGCAAGACACTTATGTTTTCA  1149
     |||||||||| | ||||||||||||||||||||||||||||||||||||||
1099 CGGTCTAGAGAGGGCAAGATCATATGGATGGCAAGACACTTATGTTTTCA  1148

1150 CCAAAGCAATGGGTGAGATGATGATCAATAGCACTCGAGGAGACGTACCT  1199
     ||||||||||||| || |||||||||||||||||||| |||| ||||||||
1149 CCAAAGCAATGGGAGAAATGATGATCAATAGCACTAGAGGGGACGTACCT  1198

1200 GTTGTTATTATAAGGCCTAGCGTCATCGAAAGCACTTACAAAGATCCTTT  1249
     || ||||||||||||||||||||||||||||||||||||||| || |||||
1199 GTGGTTATTATAAGGCCTAGCGTCATCGAAAGCACTTACAAAGACCCTTT  1248

1250 CCCTGGATGGATGGAAGGAAACAGGATGATGGATCCTATAGTTTTATGTT  1299
     |||||||||||||||||||||||||||||||||||||||||||| | ||||
1249 CCCTGGATGGATGGAAGGAAACAGGATGATGGATCCTATAGTGCTGTGTT  1298

1300 ACGGGAAGGGGCAACTCACGGGGTTTTTGGTTGATCCAAAAGGAGTTCTT  1349
     | || || || || ||||| ||||| ||||||||||||||||||||||||
1299 ATGGAAAAGGACAGCTCACAGGGTTCTTGGTTGATCCAAAAGGAGTTCTT  1348

1350 GATGTAGTTCCTGCTGATATGGTTGTTAATGCAACGTTAGCTGCTATAGC  1399
     ||||| |||||| ||||||||||| |||||||||| || ||||||||||||
1349 GATGTGGTTCCGGCTGATATGGTCGTTAATGCGACATTAGCTGCTATAGC  1398
```

FIG. 5.III

```
1400 AAAGCATGGAATGGCAATGTCAGATCCGGAACCTGAAATAAACGTGTATC 1449
     ||||||||||||||| | | ||||| | |||||||| ||||||||||||||
1399 AAAGCATGGAATGGCTAAGGCAGATACAGAACCTGAGATAAACGTGTATC 1448

1450 AGATCGCTTCTTCGGCGATAAACCCGCTGGTTTTCGAAGACTTAGCGGAG 1499
     |||||||||||||| ||||||||| || || |||||||| |||||||| |||
1449 AGATCGCTTCTTCAGCGATAAATCCTCTTGTTTTCGAGGACTTAGCTGAG 1498

1500 CTTCTTTATAACCACTACAAAACATCCCCATGCATGGACTCTAAAGGTGA 1549
     |||||||||||| |||||| | |||| ||||||||||||| |||||||
1499 CTTCTTTATAACCATTACAAATCTACCCCGTGCATGGACTCGAAAGGTGT 1548

1550 TCCTATTATGGTGCGTTTGATGAAACTTTTCAATTCCGTTGATGATTTCT 1599
     |||||||| ||||| ||||||||||| |||||| | ||||||||||||||
1549 TCCTATTAGGGTGCCTTTGATGAAGCTTTTCGACTCCGTTGATGATTTCT 1598

1600 CGGATCATTTGTGGAGAGATGCTCAAGAACGGAGTGGGTTGATGAGTGGT 1649
     ||||||||||||||||||||||||||||||||||||||| || |||| ||||
1599 CGGATCATTTGTGGAGAGATGCTCAAGAACGGAGTGGATTAATGAATGGT 1648

1650 ATGAGTTCAGCGGATAGTAAGATGATGCAGAAGCTAAAGTTTATATGCAA 1699
     ||| ||| ||||||||||||| | |||||||| || || || |||||
1649 ATGGACTCATCGGATAGTAAGATACTACAGAAGCTTAAATTCATTTGCAA 1698

1700 GAAATCTGTTGAACAAGCCAAACACCTTGCTACTATTTATGAGCCATACA 1749
     ||||||| |||| |||||||||||||||||| ||||||||||||||||||
1699 GAAATCTATTGAGCAAGCCAAACACCTTGCCACTATTTATGAGCCATACA 1748

1750 CTTTCTATGGTGGAAGATTTGATAACAGCAATACACAGAGATTAATGGAG 1799
     |||||||||||||||||||||||||||||||||||| |||||||||||||
1749 CTTTCTATGGTGGAAGATTTGATAACAGCAATACACATAGATTAATGGAG 1798

1800 AATATGTCAGAGGACGAGAAGAGAGAATTTGGATTTGATGTTGGAAGCAT 1849
     |||||||| || || |||||| || ||||| ||||||||||||||||
1799 AATATGTCTGAAGAAGAGAAGCTTGAGTTTGGGTTTGATGTTGGAAGCAT 1848

1850 TAACTGGACGGACTACATTACAAACGTTCACATTCCCGGTTTAAGAAGGC 1899
     ||||||||  ||||||||||||||| |||||||||||||||||||||| |
1849 TAACTGGAATGACTACATTACAAATGTTCACATTCCCGGTTTAAGAAGAC 1898

1900 ATGTCTTGAAAGGAAGAGCTTTA 1922     ms2
     ||||  |||||||||| ||||
1899 ATGTTTTGAAAGGAAGGGCTTAG 1921     C103
```

Nucleotide identity

Leader plus coding 87.5%

Coding only 89 %

Leader only 44.5 %

METHOD FOR THE PRODUCTION OF MODIFIED PLANTS

FIELD OF THE INVENTION

This invention relates to the production of plants having one or more desired phenotypic traits. In particular embodiments, the phenotypic trait is male sterility, and so the invention relates in those embodiments to male sterile plants, which are useful in hybrid seed production, and to the production of such plants.

Various routes for high level expression of foreign genes in plant cells have been explored over the years. Increasing levels of transcription using strong promoters have been obtained; promoters available include DNA virus promoters (such as p35S from CaMV; Fang et al, *The Plant Cell* 1 141–150 (1989)), plant gene promoters (such as EFE1α; Curie et al, *Plant Molecular Biology* 18 183–1089 (1992)) and bacterial promoters (such as pMAS; Fox et al, *Plant Molecular Biology* 20 219–233 (1992)). These promoters give high level of transcription and expression in many tissues (including leaves, stems, roots, flowers and seeds) of the plant. They are sometimes called constitutive promoters. Other promoters confer better expression in particular tissues (for example, the MAS promoter transcribes genes more efficiently in wounded tissues).

For certain applications, the expression of a gene is desired only in particular tissues or at a particular period of the plant development; for example to increase the level of expression of a heterologous protein, it is useful to express the gene specifically in seeds, as seeds are the principal organ for protein storage in plants. Expression of genes in certain tissues or organs of the plant or at a precise stage of plant development generally requires tissue-specific promoters. Seed-specific promoters have been characterised (for example, the promoter of the β-conglycine gene: Chen et al, *The EMBO Journal* 7 297–302 (1988) and Calgene's EP-A-0255378), as have root-specific promoters (such as the *Agrobacterium tumefaciens* roll promoter: Leach and Aoyagi *Plant Science* 79 69–76 (1991)).

Seed-specific promoters have been used to express pharmaceutical proteins in plant seeds (Vandekerckhove et al, *Bio/Technology* 7 929–932 (1989)). Stable expression of a gene under the control of seed-specific promoters has been obtained, and heterologous proteins were expressed, only in seeds, at a high expression level. Plants recovered from those seeds expressed the gene in their seeds, and the phenotype was transmitted from progeny to progeny.

In the production of industrially or pharmaceutically useful proteins, or other heterologous proteins, under the control of constitutive or seed-specific promoters in plants, F1 seeds will be sold to farmers to grow the plants and to produce seeds which will contain the protein of interest. In this system of production, the F1 line which expresses the gene of interest is grown by farmers and can be multiplied or reproduced by growers themselves or by competitors. Moreover, if the plant breeding industry should become required by law to control the distribution of all seeds sold, the fact that the above production process does not prevent the dissemination of genetically modified plants becomes a very significant issue.

From the above, it is apparent that there is a need for hybrid plants which (i) have a desired phenotypic trait as a result of the expression of a certain gene (or suite of genes), and (ii) are the result of a cross between two parents, neither of which have, either at all or to a substantial degree, the phenotypic trait in question.

However, the provision of such plants is not the whole extent of the problem, as there are some phenotypic traits which result from the non-expression of a gene (or suite of genes. One trait which may be (but is not necessarily) the result of non-expression of a gene is male sterility.

Hybrid seed production involves the cross of two different plants. Because most crops are able to self-pollinate, the female parent in the cross must be prevented from self-pollinating ("selfing") so that it will yield 100% of hybrid seeds. This has been achieved in several different ways:

(a) by mechanically removing or chemically inactivating the pollen-producing organs of the female parent before they reach maturity; this method has been used for example in maize (corn) and tomato;

(b) by using cytoplasmic male sterile (CMS) mutant plants; this method has been used for example in oilseed rape and sunflower;

(c) by using a recessive nuclear male sterile mutant plant; and (d) by using a dominant nuclear male sterile genetically engineered plant (artificial male sterility or AMS) as described for example in Mariani et al, *Nature* 347 737–741 (1990) or in Worrall et al, *The Plant Cell* 4 759–771 (1992).

There are practical difficulties with each of the above. Mechanical male sterilisation ((a) above) is easy and flexible. But it is labour intensive, costly and also prone to human error, giving a problem of quality of hybrid seeds batches. It is practical only for species where the flower is big enough to be emasculated manually; it is not practical, for example, for most cereals. An attempt to overcome this difficulty and reduce costs is by using chemical instead of mechanical emasculation. The efficiency of this technique is very dependent on environment conditions at the time of spraying the gametocide, and leads the seed producer to take a considerable risk each season. The cost of the gametocide and the spraying is also significant.

Cytoplasmic male sterility ((b) above) is very convenient, and allow easy maintenance of the female line. But its use is limited by availability of the appropriate mutant plant in each species of interest. The loss of cytoplasmic genetic diversity when all breeders use the same cytoplasm in their breeding program can be a serious problem as seen in the U.S. on maize in the 1970s. And the maintenance of sterility relies on the existence of a maintaining cytoplasm.

Recessive nuclear male sterility ((c) above) is not practical. Because the male sterility gene is recessive, maintenance of the male sterile line involves screening the ¼ of male sterile plants out of ¾ fertile in the selfed progeny of an heterozygous plants. In the absence of a tightly linked selectable or easily screenable marker this is practically impossible. This is the problem that artificial male sterility has tried to solve.

Artificial male sterility ((d) above) has solved the problems of the other systems but only to some extent. The AMS gene system is potentially universal, being limited only to genetically transformable species. It does not rely on the existence of a mutant as in CMS. The maintenance of the male sterile line is obtained by engineering a dominant male sterility gene linked to a marker gene that allows selection of AMS plants in a population segregating ½ AMS plants. To be practical, this marker is often a herbicide resistance gene. But this process is undesirable for several reasons:

Agronomy: the seed production can be affected by the need to eliminate half the female plants (the fertile segregants) from the field. The result is a heterogenous plant density, and potentially lower yield and lower quality of the seeds. The cost of spraying the herbicide is significant.

Use of the herbicide: on some crops, such as vegetables, the use of a herbicide resistance gene, and the subsequent use by farmers of the herbicide is not desirable. Generally speaking, there is a tendency to restrict the use of herbicide as much as possible.

The female line can be stolen easily. Once sold on distant and not easily controllable markets, the basic seeds can be multiplied by the local seed producer without the breeder's knowledge, control or share of the profit.

Disadvantages with a conventional AMS system can be appreciated by looking at a particular example. The AMS system which is the subject of EP-A-0344029 (Plant Genetic Systems (PGS)) is based on the tissue-specific expression of a toxin gene (Ribonuclease, "Barnase") to generate the male-sterile parent for hybrid seed production. The genetic linkage of the toxin to a selection marker (herbicide resistance) provides the basis for the selection of male-sterile plants. Fertility can be restored during hybrid seed production by crossing with a male-fertile parent (restorer line) that expresses a toxin inhibitor ("Barstar").

The problem with the PGS system lies in the production of the male-sterile line, which is used as the female parent in hybrid seed production. Due to the dominant character of the toxin, the female parent has to be propagated by crossing the heterozygous line (−/+) with a male fertile line (+/+). As the toxin gene segregates, only half of the progenies (male-sterile and herbicide resistant) from this cross can be used for hybrid seed production; the other half (male-fertile and herbicide sensitive) has to be eliminated and is therefore lost for hybrid seed production.

It is the post-germination selection of male-sterile plants that the seed producer seeks to avoid for three reasons:

1. The production of the female parent is inefficient (50% loss).
2. The post-germinal selection in the field might cause heterogeneity in plant distribution in the field, which could negatively affect seed yield. Computer simulations revealed patches with a high number of plants and patches that are almost void of plants. Attempts to mitigate this problem using agricultural practices, such as planting at higher density or going through the field with machinery more often, mean extra costs for the seed producer.
3. The use of a herbicide resistance selection marker could increase the difficulty in obtaining permission to release the crop and market the product, especially for vegetables.

The maintenance problem of a dominant AMS gene has to some extent been addressed. First, a solution was proposed which involved making the AMS gene inducible (WO-A-9008830 (ICI)). In the absence of the inducer, the plant is fertile and can therefore be multiplied easily. Spraying with an inducer turns the AMS gene on and causes the plant to be sterile. This approach is widely believed to be not practical because of its sensitivity to environmental conditions at the time of spraying the inducer. The risk to the seed producer if the inducer fails to perform is enormous. This is basically no improvement on the use of gametocides.

Secondly, a proposal to solve the same problem of maintaining the female line (WO-A-9201799 (Paladin Hybrids)) describes the use of a cross to generate the female line, but relies on an inducible or conditional male sterility in the plant used as a female to perform that cross. It does not describe a workable system, only a limited set of genes which are not shown in the application to work practically.

In summary, AMS is the most satisfactory available male sterility system at the moment, but it does not provide a generally acceptable method for producing the female parent. The method involves some undesirable technology and costs, and does not protect the valuable female variety from being illegally copied. So it seems that a lot of work has been done to improve the efficiency of hybrid seeds production. Nevertheless, in order to produce hybrid seeds economically, there is still the need for a system which would associate the advantages of the above mentioned systems and overcome their limitation. In particular, the advantage of CMS in terms of maintenance and protection of the female line would be very useful in conjunction with a potentially universal system based on AMS.

More recently, there has been disclosed (EP-A-0589841 (CIBA-GEIGY)) a method of producing plants which are made sterile, the method comprising:

(a) transforming a first parent plant cell with a first expression cassette, the cassette comprising a nucleotide sequence encoding an anther-specific 5' regulatory region operably linked to a nucleotide sequence which encodes a transactivator polypeptide;

(b) regenerating a transformed plant, Parent 1, from said first transformed plant cell;

(c) transforming a second parent plant cell with a second expression cassette comprising a target nucleotide sequence which is capable of being activated by said transactivator polypeptide operably linked to a nucleotide sequence which encodes antisense RNA or a polypeptide capable of disrupting the formation of visible pollen;

(d) regenerating a transformed plant, Parent 2, from said second transformed plant cell; and (e) crossing Parent 1 with Parent 2 to obtain male-sterile offspring.

This document may represent prior art in certain states under certain circumstances.

It has now been found that it is possible by means of binary systems to solve or at least mitigate the problems discussed above.

SUMMARY OF THE INVENTION

According to a first aspect of the invention, there is provided a method for producing a plant having a desired phenotypic trait, the method comprising crossing a first line with a second line wherein each of the first and second lines lack the phenotypic trait in question and wherein at least one of the first and second lines is transgenic, with the proviso that when the desired phenotypic trait is male sterility this does not result from the action of a transactivator polypeptide on a target nucleotide sequence.

The term "transgenic", in the context of this invention, should not be taken to be limited to referring to plants containing in their germ line one or more genes from another species (plant or otherwise), although transgenic plants may contain such a gene or genes. Rather, the term refers more broadly to any plant whose germ line has been the subject of technical intervention by recombinant DNA technology. So, for example, a plant in whose germ line an endogenous gene has been deleted, duplicated, activated or modified is a transgenic plant for the purposes of this invention as much as a plant to whose germ line an exogenous DNA sequence has been added.

In certain important embodiments of the invention, the phenotypic trait is (generally artificial) male sterility. In other important embodiments, the phenotypic trait may be the production of a heterologous protein either specifically in the seed or elsewhere in the plant.

Preferably, both the first and second lines are transgenic.

The cross between the first and second lines will usually be achieved in a manner which avoids self-pollination. At least for the male sterility embodiments of the invention, because of the small scale on which it has to be performed, the non-self-pollinating cross can make use of processes which would be unacceptable for large scale commercial hybrid seeds production, like chemical emasculation for cereals. It can also be more thoroughly controlled for quality than a non-self-pollinating cross performed for commercial hybrid seeds production. The scale of a non-self-pollinating cross operation associated with the present invention will be much smaller than the current hybrid production surface since this process will be used at the basic seed's (hybrid parent) production level only; a multiplication factor of 200 (a conservative estimate for maize), for example, means that for producing hybrid seeds needed to plant 40,000 surface units of hybrid maize, only one surface unit has to be manually detasseled (say) as opposed to 200 in the present process. In the case of tomato, because the seed production process takes place in glasshouses, production of a male sterile female in accordance with the invention may involve manual emasculation of the first line and pollination with pollen from the second line, in a process similar to the one currently used to produce hybrid seeds. The scale however will be very much reduced (perhaps a thousand fold).

In relation to male sterility, the use of sufficiently fertile plants as parents of the female line distinguishes the present invention from the cryptocytotoxic AMS proposed, but not completely described, in WO-A-9201799 (Paladin Hybrids). Each of the two parents of the female line contains in the homozygous condition a gene which has no effect by itself. Combination of the two genes in the same plant, as obtained in the progeny of a cross between the two parents, create male sterility.

It is not critical that plants of the first and second lines (which in the description of preferred embodiments of the invention may be referred to as Line A and Line B, respectively) be fully fertile (or otherwise lacking the phenotypic trait sought in the hybrid progeny). In relation to fertility, it is important that they be capable of being selfed, and that in the homozygous condition they be fertile enough to be multiplied at acceptable or reasonable cost. Plants of the first and second lines can be isogenic, or different in the case of a three way hybrid. The fertility of the final product (the hybrid seed) is not always critical. For some outcrossing species (eg maize), the hybrid need not be 100% fertile. In other cases (eg tomato), in relation to male sterility embodiments of the invention, the hybrid needs to be fully fertile; a restorer gene able to restore male sterility is used.

There are a number of different ways in which the invention can be implemented. In certain embodiments of the invention, the first and second lines have the following characteristics:

(a) the first line comprises homologous or heterologous DNA which controls the desired phenotypic trait and in the first line is adapted such that the line does not have the phenotypic trait, and (b) the second line has DNA which when present in the same plant as the phenotypic trait control DNA adapts the phenotypic trait control DNA to give rise to the phenotypic trait (this may be called a sterility adapter DNA).

The phenotypic trait control DNA may be male fertility or sterility control DNA.

In this way, a gene in one of the first and second lines is capable of causing absolute male sterility (or another desired phenotypic trait) in the presence of a gene in the other of the first and second lines, both genes being present in the heterozygous condition of the hybrid progeny, which then forms the female parent in the cross to produce commerical hybrid seeds.

The male sterility control sequence in the first line may comprise a sequence which, when expressed, confers male fertility on the plant. In these circumstances, the male sterility control sequence is expressed in the first line, which is therefore phenotypically normal (at least in respect of male sterility). The sterility adapter DNA of the second line would then act to prevent (at least partially) expression of the sterility control sequence in a hybrid. These embodiments of the invention may be said to involve inactivation of an "active" artificial male sterility gene.

For example, the first line may comprise (i) two genes, designated ms and ms*, respectively, expression of at least one of which is needed for male fertility and (ii) a prevention or disruption sequence (such as DNA encoding a ribozyme, designated $R_{ms}$, or DNA encoding antisense RNA, designated $A_{ms}$, specific for ms) which prevents or disrupts the proper expression of the ms gene.

This line will be male fertile, by virtue of the expression of ms*, which is not disrupted by the ribozyme $R_{ms}$ or the antisense $A_{ms}$. The second line will in these circumstances comprise (i) the two genes, designated ms and ms*, respectively, expression of at least one of which is needed for male fertility and (ii) a prevention or disruption sequence (such as DNA encoding a ribozyme, designated $R_{ms*}$, or DNA encoding antisense RNA, designated $A_{ms*}$, specific for ms*) which prevents or disrupts the proper expression of the ms* gene.

This line, too, will be male fertile, by virtue of the expression of ms, which is not disrupted by the ribozyme $R_{ms*}$ or the antisense $A_{ms*}$. When the two lines are crossed, the resulting plant will be male sterile, as the proper expression both the ms and the ms* genes is disrupted. Male fertility may be restored by the expression of a third male fertility gene ms** which is resistant to both ribozymes $R_{ms}$ and $R_{ms*}$ (or the corresponding antisense or other disruptors).

This embodiment of the invention is not limited to the use of ribozymes and antisense. Any DNA which directly or indirectly disrupts or prevents, in a sufficiently specific manner, the proper expression of the appropriate male fertility gene (ms or ms*) can be used. Examples of male fertility genes ms or ms* include ms2-C103 (Aarts et al, *Nature*, 363: 715–717 (1993), APRT (Moffatt et al, *Plant Molecular Biology*, 18: 653–662 (1992)) and any other suitable natural or artificial male fertility-controlling gene, which may for example be identified by mutation studies. The designation "ms" or "ms*" is not intended to be limited to any particular gene, whether natural or artificial.

Parenthetically, it should be noted that in this application, unless the context requires otherwise, the use of the word "gene" simply denotes a transcribable or expressible DNA sequence and is not limited to mean an exact replica of an expressible genomic DNA sequence (although that may be preferred in certain circumstances); it is to be understood, therefore that synthetic DNAs, cDNAs and "minigenes", which contain some, but not all, of the introns in a naturally occurring gene, are within the scope of the term. Also within the term are DNA sequences which are transcribable to RNA but not necessarily subsequently translated to protein; such DNA sequences may encode antisense RNA and ribozymes.

Another type of system involving inactivation of an "active" artificial male sterility gene is as follows. The first line contains:

(i) an expressed gene giving rise to artificial male sterility; this gene may for example be the ribonuclease Barnase (from *Bacillus amyloliquefaciens*; Paddon et al, *J. Bacteriol.* 171 1185–1187 (1989)) driven by a tapetum-specific promoter, such as one of those designated A3 and A9 (WO-A-9211379); and (ii) an expressed restorer gene which restores male fertility; in the case of Barnase, this may be the Barstar toxin inhibitor (Hartley *Trends in Biochemical Sciences* 14 450–454 (1989)).

The first line will be male fertile because the Barstar (or other restorer) restores male fertility in spite of the expressed Barnase. The second line contains:

a repressor gene, which represses the activity of the restorer gene (which may be for example a gene encoding a ribozyme or antisense to Barstar).

A hybrid formed by crossing the first and second lines will be male sterile, as the repressor gene will prevent the restorer gene from functioning, and therefore the artificial male sterility gene will itself function.

Another major group of embodiments within the invention involves the use, in one of the lines, of an inactivated phenotypic trait (for example, artificial male sterility) gene. The gene becomes active on crossing with the other line.

First, within this group, is the case where a stop codon (or more than one stop codon) in a gene responsible for a desired phenotypic trait (such as a dominant AMS gene) in the first line is suppressed. The first line contains an AMS gene, or other phenotypic trait gene, coding for a protein; the gene is inactivated by one or more nonsense mutations, which may be the same as or different from each other. The second line contains a gene or genes coding for one or more suppressor tRNAs; these are designed to suppress the nonsense mutation(s) in the phenotypic trait (eg AMS) gene of the first line.

For practical reasons, if more than one mutation is needed in the AMS or other phenotypic trait gene of the first line, the mutations might all be identical, so that only a single type of suppressor tRNA is needed in the second line. Several copies of the tRNA gene can be used, if desired.

The genes can be introduced in plants by transformation (as may other foreign genes useful in this invention). In a simple implementation of this embodiment, the transformants have no phenotype which could be used to tell that the tRNA suppressor gene is working properly. This is inconvenient, because of the large variability of transgene expression between primary transformants due to position effects. However, for minimising any problem that there may be on this count, a reporter gene (such as a glucuronidase (GUS) gene inactivated by the same nonsense mutation as the male sterility or other phenotypic trait gene) may be linked to, or at least provided with, the suppressor tRNA gene so that the level of suppression in transfonnants of the second line can be evaluated. If the suppressor gene is functioning properly, the nonsense codon in the GUS gene will be suppressed and detectable glucuronidase will be expressed.

Transformants of the first line can be evaluated by performing the cross with the second line and screening for sterility, or another phenotypic trait, in the hybrid.

Restoration of fertility in a commercial hybrid male sterile plant can be achieved by a gene suppressing the AMS gene activity either at the protein level (such as Barstar for Barnase) or at the transcription/translation level (such as ribozymes or antisense).

In more detail, a preferred implementation of an embodiment of the invention such as this and relating to male sterility is as follows. The first line (Line A) will express from the A9 promoter (which is tapetum specific and the subject of WO-A-9211379) a mutated barnase gene. The mutation will be introduced by in vitro mutagenesis. The mutation will change into an amber translational stop codon either the codon for isoleucine or the codon for tryptophan at position 4 or 35, respectively, of the mature barnase protein sequence. (This numbering does not take into account the artificial methionine codon introduced 5' during cloning of the ORF coding for the mature barnase protein.) The gene used in this embodiment is described in WO-A-9211379 and Paul et al. *Plant Mol. Biol.* 19 611–622 (1992). All alterations refer to published sequences (from *B. amyloliquefaciens*; Paddon et al, *J. Bacteriol.* 171 1185–1187 (1989)) with Genbank accession number M14442.

The second line (Line B) will express an amber suppressor tRNA which, when crossed to Line A, will insert at the artificial amber stop codon (UAG) of the barnase mRNA either a leucine or a tryptophan into the amino acid sequence. In the case of the leucine suppressor, the primary amino acid sequence of the active toxin will be different from the published one (isoleucine→leucine). The suppressor tRNAs will not allow (or at least reduce the occurrence of) a read through at the naturally occurring ochre translational stop codon (UAA) of the barnase mRNA.

The suppressor tRNA-leucine gene can be constructed in vitro from artificially made oligonucleotides according to the published sequence (Green et al, *Plant Mol. Biol.* 10 13–19 (1987); Genbank accession number M21542) of the tRNA-leu3 gene from *Phaseolus vulgaris*. The construction process directly yields the amber-suppressor gene where the anticodon sequence is changed from CAA to CUA.

The suppressor tRNA-tryptophan gene can be built by first isolating the wild type tRNA-tryptophan2 gene of *Arabidopsis thaliana* (Lin et al, *Plant Mol. Biol.* 18 159–160 (1992); Genbank accession number: X5793) by DNA amplification from genomic DNA. The isolated gene will be converted by in vitro mutagenesis into an amber-suppressor gene where the anticodon sequence is changed from CCA to CUA.

Both suppressor tRNA genes can be expressed constitutively from their own (internal) promoter. To select the lines that express a functional amber-suppressor tRNA, an amber-mutated GUS gene transcribed from the cauliflower mosaic virus (CaMV) 35S promoter will be linked to the respective suppressor gene. Expression of GUS may thus allows the evaluation of the suppressor activity in the primary transformants of line B.

Lines A and B, respectively, can be obtained and propagated as homozygous lines. When crossed to each other, the resulting F1 offsprings, however, will be male-sterile due to tapetum-specific expression of an active barnase protein.

The invention, particularly in this embodiment, is not limited to the use of barnase as an AMS gene; other AMS genes can be used. AMS genes encoding very active proteins are preferred, since it can be assumed that efficiency of suppression may be low and so will the level of functional protein in the hybrid A×B. Codons other than Ile or Trp can be mutated, provided an efficient suppressor tRNA gene can be made. Other stop codons (ochre or opal) can be used, provided efficient suppressor tRNA genes can be made.

Many plant nuclear tRNA gene sequences are publicly available and choice could be made between them; construction of an appropriate tRNA gene could be by using synthetic DNA deriving the sequence from the chosen public sequence and changing the anticodon, for example by cloning from genomic DNA and normal gene using PCR technology and mutating the anticodon by in vitro mutagenesis.

It is expected that not all combinations of a mutation in an AMS gene and a suppressor tRNA would be efficient, and some routine experimentation could be necessary to choose between combinations. Such evaluation can be done as described in the examples below. In particular the efficiency of the stop signal used in the AMS ORF in the first line should be evaluated; the AMS should have an effect on fertility low enough for the plant to be at least partially fertile. The efficiency of stop suppression provided by the chosen suppressor tRNA gene should also be evaluated; the activity of the AMS gene in the presence of the suppressor gene should be high enough to cause sufficient male sterility; therefore the use of a very active AMS gene is recommended.

To demonstrate the feasibility of this approach, it is of interest to note that, in unrelated work, Carneiro et al, *Plant Mol. Biol.* 22 681–690 (1993) have shown that the in planta expression of their suppressor tRNA$_{amber}$-leu3 gene alone had no deleterious effect on either growth or fertility of the transgenic tobacco plants. The authors also detected in protoplasts from those plants significant (20% of GUS+ controls) suppression of electroporated GUS genes that contained amber mutations. The suppressor tRNA$_{amber}$-tryptophan2 was demonstrated by Franklin et al, *The Plant Journal* 2 583–588 (1992) to suppress an amber-mutated CAT (Chloramphenicol Acetyl Transferase) gene (up to 10% of CAT+control) when co-electroporated into carrot protoplasts. Although the level of suppression seems to be "very low" in transgenic plants (W. R. Folk, personal communication) as compared to protoplasts, it is expected in the present embodiment of the invention to be sufficiently high for toxins such as the barnase of which only one molecule is supposedly lethal for the cell in which it is expressed.

Another embodiment within the group involving the inactivation of a gene is based on transactivation of the expression of the gene. The gene may be an artificial male sterility gene, or it may code for (or at least control) a phenotypic trait of interest. This embodiment of the invention is particularly suitable for expressing genes encoding heterologous proteins, particularly high value proteins, of interest. This embodiment of the invention, among others, is also suitable for expressing genes giving rise to organ ablation.

In particular, the AMS or other (eg heterologous) gene is present in the first line but under the control of regulatory sequences (such as a promoter) which cannot function (either at all or sufficiently) for significant expression of the gene in the first line. In the second line is a gene which, when present in the same plant as the AMS or other (eg heterologous) gene with its associated regulatory sequences, allows those regulatory sequences to function sufficiently to cause significant expression of the AMS or other gene. For example, the regulatory sequences in the first line may comprise a promoter which does not function with endogenous RNA polymerase (such as the promoter from phage T7), and a gene encoding an RNA polymerase (which would be T7 polymerase in the specific case illustrated) which does function with the promoter may be present in the second line. For efficient use in eukaryotic cells the phage T7-RNA polymerase protein (T7RNP) should be modified so that it is targeted to the cell nucleus. This has been achieved in plant cells (Lassner et al, *Plant Molecular Biology* 17 229–234 (1991)) by the addition of a nuclear-targeting signal from the large T-antigen of SV40 to the N-terminus of T7RNP.

This embodiment of the invention is particularly well suited to the production of a protein encoded by a heterologous gene of interest, in the seed or other parts of hybrid F1 plants. Hybrid cells expressing the heterologous gene result from crosses between a first parental (eg female) line, designated line A, which contains the heterologous gene under the control of the bacteriophage T7 promoter, and a second parental (eg male) line, designated line B, which constitutively expresses the T7 RNA polymerase. Neither line A nor line B expresses the heterologous gene of interest. The heterologous gene is expressed in F1 seeds harvested on line A, though, and is expressed constitutively in F1 plants grown from those seeds. F1 seeds expressing the heterologous gene can be harvested for the processing and purification of the heterologous gene product. This binary system is typically adapted for expression of high added value compounds. Growers who cultivate line A and line B grow only non-expressing plants, and so the system is susceptible of a high level of control.

To describe a particular embodiment in greater detail, a heterologous gene is under the control of the bacteriophage T7 promoter in the first line (line A). The heterologous gene is not expressed in plant cells in line A, as the T7 promoter normally does not contain a binding site for plant RNA polymerase. In animal cells, non-specific transcription of T7 polymerase has been observed (Lieber et al, *Methods in Enymology* 217 47–66 (1993)); if any non-specific transcription of the heterologous gene should occur in the plant, it is possible to suppress this non-specific transcription by the use of modified T7 promoter. The modification may be one or more mutations in T7 promoter which block plant RNA polymerase transcription without modifying transcription mediated by the T7 RNA polymerase. These kinds of mutation in T7 promoter sequences have been made to prevent transcription of T7 by RNA polymerase of animal cells (Lieber et al, *Methods in Enzymology* 217 47–66 (1993)).

The other parent in this embodiment is a transgenic, homozygous line, designated line B, which constitutively expresses T7 RNA polymerase in all tissues and organs, particularly in endosperm and embryo tissues; expression is stable and transmitted through progenies. The T7 RNA polymerase may be under the control of a viral promoter, such as the p35S promoter from CaMV, a plant promoter, such as EF1α, or a bacterial promoter which is transcribed in plant cells (such as MAS). A suitable promoter may be the plant aconitase promoter. The T7 RNA polymerase gene contains, at the N-terminal or C-terminal end of the coding sequence, a nuclear location signal (NLS) sequence. The function of the NLS sequence is to direct expression of T7 RNA polymerase to the nucleus. The NLS sequence may be a nucleotide sequence which codes for the subsequence Pro-Lys-Lys-Lys-Arg-Lys-Val of the large antigen of SV40; this subsequence has been shown to be sufficient to target T7 RNA polymerase to plant nuclei (Lasner et al, 1991).

Plants are obtained by crossing transgenic line A and transgenic line B. Various techniques can be used to ensure a specific cross between line A and line B, including: artificial male sterility systems, cytoplasmic or nuclear male sterility, and manual or chemical sterilisation of the female line. Pollen from the male line will fertilise the female line. Seeds which contain the expression product of the heterologous gene will be harvested on the female line.

Expression of the heterologous gene is restricted to tissues coming from fertilisation, namely the zygote and the endosperm. There is no expression in tegument or maternal tissues. In zygotic tissues (cotyledons, roots and apices) and endosperm of the F1 seeds, the 17 RNA polymerase, which is expressed in the nucleus, specifically recognises the T7 promoter and transcribes the heterologous gene of interest to form mRNA. T7 RNA polymerase, when functional, allows a high level and stable gene expression in seeds. If F1 seeds are germinated and grown, the heterologous gene is expressed in all tissues and organs of the plant, particularly in cotyledons, young plantlets, roots, leaves, stems and flowers.

The heterologous gene may be a mammalian or microorganism gene encoding a protein, for example for pharmaceutical or cosmetic use. However, the invention is not at all limited by the purpose or function of the expression product of the heterologous gene. For example, the heterologous gene may encode an industrial protein such as an enzyme or other bio-product; or the heterologous gene may encode an enzyme for use in situ to produce a substance of interest or to modify the primary or secondary metabolism of the plant to produce an added value compound.

It is equally contemplated in the present invention that the heterologous gene may not have a protein expression product. For example, the heterologous gene may be a gene coding for antisense RNA or a ribozyme. Antisense RNA and ribozymes may for example, like enzymes discussed in the preceding paragraph, modify the metabolism of the plant, or the content or nature of plant molecules such as polysaccharides or fatty acids, to produce food or feed with nutritional or other economic benefits or to produce plants for industrial, agricultural or environmental uses.

Another example of the present category of embodiments would be the use in one line of a promoter for the AMS (or other heterologous) gene which is not active in the absence of its cognate trans-acting transcription factor; in the second line would be a tissue-specific gene encoding the trans-acting transcription factor.

In the embodiments of this group which relate to male sterility, restoration of male fertility can be achieved, as described above, by suppressing the AMS activity.

A third embodiment within the group involving the inactivation of an active artificial male sterility gene, or other heterologous gene, is based on transactivated specific splicing of an inactivating sequence (such as an intron) placed in the gene in question.

In this embodiment, the first line, Line A, contains a gene of interest, such as an AMS gene, interrupted by an inactivating sequence which is capable of being spliced out. The inactivating sequence may be an intron or any other sequence which is capable of being spliced out by, say, a maturation enzyme. The intron may be a yeast mitochondrial intron, such as a derivative of the intron bI4 of the *Saccharomyces cerevisiae* cytochrome b gene. In another implementation of this embodiment, the intron may be the rRNA group I intron from *Neurospora crassa*, which is spliced by the protein CYT18. The gene of interest is inactivated by the intron.

The second line, Line B, contains a gene encoding an enzyme capable of splicing out the inactivating sequence. In the specific case of the yeast mitochondrial intron discussed above, the enzyme would be the corresponding yeast maturase (eg the coding sequence from intron bI4 as above), engineered to have the universal genetic code, to have a nuclear localisation signal, and expressed in the same tissue as the gene of interest. As a generality, the maturase has no effect on the plant, so phenotypic normality is preserved. In the hybrid A×B, the intron is spliced by the maturase and the gene of interest is functional. In the case of the rRNA group I intron, the gene needed for splicing encodes the CYT18 protein, as has been described.

For male sterility embodiments, restoration of male fertility can, as described above, be achieved by suppressing the AMS activity.

In another important embodiment, the desired phenotypic trait is seed specific expression of one or more proteins. This can be useful for the production of pharmaceutically useful proteins in seeds. Examples of such pharmaceutically useful proteins include lymphokines, EPO, tPA, interferons, blood factors and/or enzymes.

In another embodiment, the phenotypic trait results from the non-expression of a gene. This can be brought about when, for example:

(i) the first line comprises an antisense sequence for the gene whose non-expression gives rise to the phenotypic trait, the antisense sequence being under the control of a promoter or other regulatory sequence which cannot function for significant expression of the antisense sequence; and (ii) the second line comprises a gene which, when present in the same plant as the antisense sequence with its associated regulatory sequence, allows that regulatory sequence to function sufficiently to cause significant expression of the antisense sequence, such expression leading to down regulation of the gene whose non-expression gives rise to the phenotypic trait.

Plants obtainable using the methods of the invention form a second aspect of the invention.

Artificially male sterile plants produced using the methods of the invention are the result of a cross between two normal fertile, homozygous plants referred to above as the first line and the second line (or, in specific embodiments, Line A and Line B). This cross between the first and second lines would have to be performed in a manner to prevent self-pollination, but only on the small scale needed to produce the basic seeds. Self-pollination can be prevented by using chemical, mechanical or manual castration of one line and physical separation in the field of the other line (the pollinator). Careful examination of the hybrid seed production process leads to the conclusion that a manual cross at the basic seeds production step is practical and economical. The cost of crossing manually is largely overcome by the advantages of obtaining a genetically homogenous batch of (male sterile) female parent seeds which can be used directly in the hybrid seeds production field, without selection, and which cannot be easily reproduced. An added advantage is that this cross could be the cross of a breeding scheme (as in 3-ways hybrids commonly used), in which case there is no added cost beyond that of the normal basic seed production process.

Similar considerations apply, *mutatis mutandis*, to other plants of the invention having different phenotypes.

Heterologous DNA can be introduced in the desired plant by transformation, and the transgenics are bred to homozygosity. Preferably, DNA is transformed into plant cells using a disarmed T1-plasmid vector and carried by Agrobacterium by procedures known in the art, for example as described in EP-A-01 16718 and EP-A-0270822. Alternatively, the foreign DNA could be introduced directly into plant cells using an electrical discharge apparatus. This method is preferred where Agrobacterium is ineffective, for example where the recipient plant is monocotyledonous. Any other method that provides for the stable incorporation of the DNA within the nuclear DNA of any plant cell of any species would also be suitable. This includes species of plant which are not currently capable of genetic transformation.

Although the usefulness of the invention is not especially limited to any particular species or other taxonomic grouping, it is expected that the greatest use of the invention will be with economically important crops. Examples include maize, tomato and wheat.

Male sterile plants in accordance with the invention are useful as female parents in the production of commercial F1 hybrid seed. The precise details for this final cross will vary from crop to crop. For maize, the male parent (designated plant C) will be planted in one row alternating with several rows of female parent (designated plant AB). After pollination the male parent rows are crushed, and seeds harvested only from the female rows. No chemical treatment of the production field is needed, and except for the absence of manual detasseling, the process is very similar to the one currently used in the field.

The female parent cannot be reproduced since it is made through a cross that the hybrid seed producer cannot perform. The hybrid seeds obtained (designated ABC) will segregate male sterility. The actual frequency of male sterile plants in the hybrid seeds population will depend on the location of the heterologous DNA in the genomes of the first and second lines, as described above. The highest frequency of male sterile would be if the two heterologous genes segregate independently (are located on different linkage groups); it would then be 25%. Because wind driven cross pollination is very efficient in maize, in practical terms the population would behave as a 100% fertile population, and a restorer gene in parent C is not compulsory. If it is however desired, it can be done as described below for tomato.

In the case of tomato, male sterile seeds in accordance with the invention can be planted in a hybrid seed-production glasshouse as the female parent (plant AB), and pollination by pollen from the male parent (plant C) is done. No chemical treatment, no sorting of plants, and no emasculation are needed. In this case, the hybrid plants obtained should preferably be 100% fertile since cross pollination is not very effective naturally in the tomato production field. To achieve that, it is possible to rely on two techniques. First, in a genetic approach, the heterologous DNA in plant A (gene A) and the heterologous DNA in plant B (gene B) are located at tightly linked loci on opposite chromosomes of a given pair, and therefore have very little probability of cosegregating in the hybrid plant (as explained in WO-A-9201799). Secondly, plant C may be engineered to express a restorer gene; any dominant gene which prevents gene A or gene B activity is suitable. A gene expressing Barstar (a proteinaceous inhibitor of Barnase (Hartley *Trends in Biochemical Sciences* 14 450–454 (1989)) is appropriate (see for example EP-A-0412911).

To obtain a phenotype using the described binary systems, one combines the two genes in the same plant by crossing two plants, usually primary transformants or selfed progeny of primary transformants. Because of the well known "position effect", not all primary transformants containing the first gene will be suitable for crossing to all primary transformants containing the second gene, and parent plants will generally have no conveniently detectable phenotype allowing to screen the suitable plants among them. To identify the suitable parents among the independent primary transformants, many crosses are performed, and the hybrids obtained are then evaluated for the desired phenotypic trait. Although this can be done, it is a lengthy process. One way to implement the invention more quickly is the following:

Target plant tissue is transformed with the first gene, but not allowed to regenerate into plants. The regeneration capacity of the tissue is retained. The transformed tissue is then transformed with the second gene, using a different selectable marker if needed. The transformed tissue, now containing the two genes at independent positions in the genome, is then allowed to regenerate a whole fertile plant. Among the plants obtained in that way, some will have the desired phenotypic trait as a consequence of them having the two genes at suitable positions in the genome. In the progeny of such a plant, segregation plants having only the first gene or only the second gene and not having the desired phenotypic trait can be identified. Such plants are then multiplied and used as parents in the cross to produce the hybrid plant with the desired phenotype. If an extensive back-cross process is required to convert the primary transformant to a better agronomic variety, as is often the case for example with maize, this back-cross process can be done on the plant containing the two genes and showing the phenotype. When an acceptable elite variety is obtained, usually after 3 to 6 steps of back-cross, the two genes are allowed to segregate and the parent plants are identified among the segregants. The parent plants are then multiplied, and later used to produce the desired hybrid plant, showing the desired phenotype. If, however, it is desired that the two parents are different, the back-cross process can be done using a different recurrent pollinator on each parent (having one of the two genes and not showing the phenotype) and not on the original transformant (having the two genes and showing the phenotype).

Plants useful as either the first or second lines, as used in the methods of the invention, form a further aspect of the invention.

According to another aspect of the invention, there is provided propagating material, particularly seed, of a plant in accordance with the invention.

According to a fifth aspect of the invention, there is provided a hybrid plant obtainable by crossing a male plant with a male-sterile plant in accordance with the invention.

In yet a further aspect of the invention, there is provided a method of producing a plant having a desired phenotypic trait, the method comprising crossing a first line and a second line wherein each of the first and second lines does not have the phenotypic trait in question, and wherein at least one of the first and second lines is transgenic.

Among the phenotypic traits that could be created using some of the binary systems that we describe, a useful trait is cell ablation.

Some plant tissues or organs can be undesirable. Examples of these include seeds in fruits (grapes), hair on fruit skin (peaches), or petals in oilseed rape (as they promote propagation of the pathogenic fungus sclerotinia). However, in many cases it would be desirable to limit this trait to hybrid plants, produced by crossing parents with no altered phenotypes.

This can be achieved by using a binary system made for example of an inactive toxic gene under control of a promoter specific of the tissue or organ to be destroyed, supplied by the first parent plant, activated in the hybrid plant by the activator gene supplied by the second parent.

Preferred genes are the Barnase ORF inactivated by one or more stop mutation, under control of the appropriate tissue specific promoter, and a suppressor tRNA gene able to read the stop codons.

Another example of a suitable system consists of a non-expressed toxic gene supplied by the first plant, which expression is activated in the hybrid in a tissue specific manner by a tissue specific transactivator supplied by the second parent.

Preferred genes are the Barnase ORF under control of a suitably modified T7 promoter, and a T7RNA Polymerase gene under control of a promoter specific for tissue to be destroyed. Another possibility of the same example is to use the CaMV translational transactivator (gene VI) under control of a tissue specific promoter to activate translation of a toxic ORF present as the second cistron in a mRNA expressed in the tissue to be destroyed. Another possibility relies on intron splicing using a tissue specific maturase as explained previously.

Preferred features for each aspect of the invention are as for each other aspect, *mutatis mutandis*.

BRIEF DESCRIPTION OF THE DRAWINGS

Figure 1A:
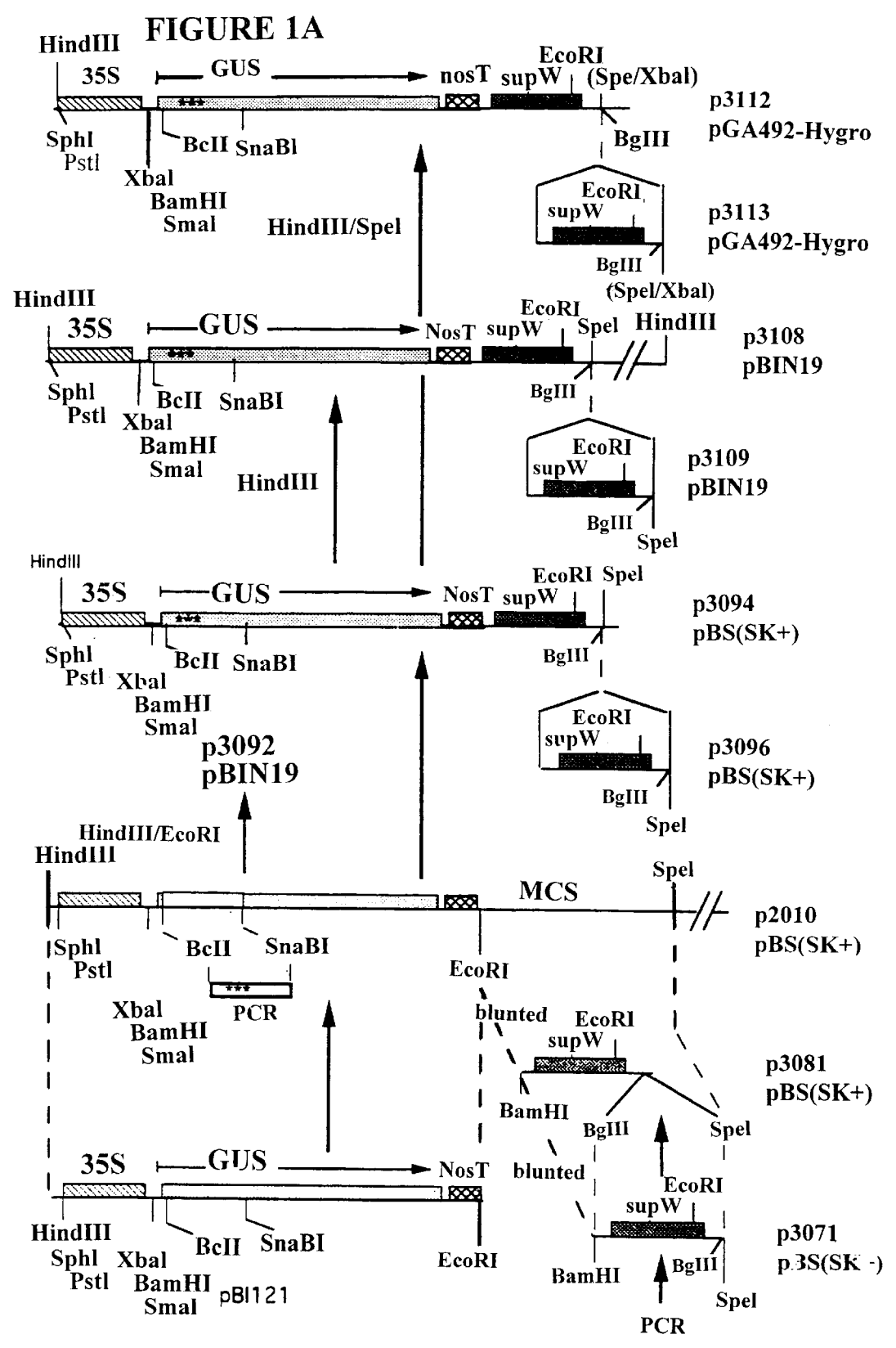

FIG. 1A: shows the scheme for cloning transactivator reporter gene;

FIG. 5(I–III): shows the alignment of *A. thaliana* ms2 (SEQ ID NO:21) with *B. napus* C103 (SEQ ID NO:22) DNA.

DETAILED DESCRIPTION OF THE INVENTION

Figure 1B:
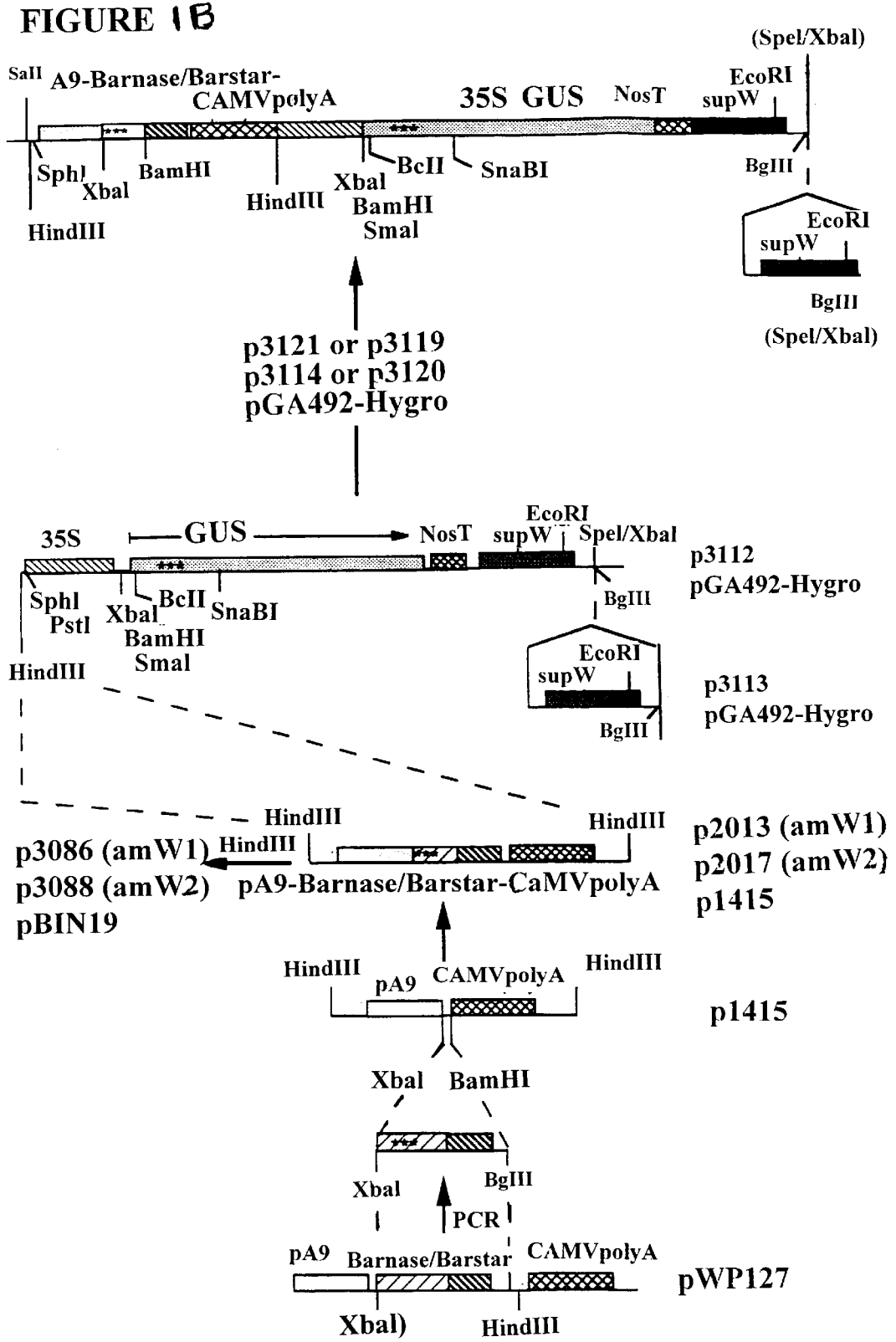
FIG. 1B: shows the scheme for cloning the AMS mutant genes.

EXAMPLE 1 tRNA Mediated Suppression of a Stop Codon in an AMS Gene

A suitable Artificial Male Sterility (AMS) gene coding for a protein which prevent male fertility can be made inactive by substitution of 1–3 bases in the coding sequence (Open Reading Frame ORF) so that a valid codon is transformed into a Stop codon (TAA: ochre, TGA: opal, TAG: amber). This mutated gene (gene A) is therefore inactive and plants containing it (plant A) are fertile. A suppressor tRNA can be engineered which will read the Stop codon as an amino acid codon and therefore allows translation of the mutated ORF. This gene (gene B) in itself will have no effect on the plant that expresses it (plant B) as shown for example in tobacco by Carneiro et al., (*Plant Mol. Biol.* 22 681–690 (1993)). The product of a cross between A and B will express the AMS ORF and be sterile.

Specifically, the codon coding Trp at amino acid position 37 of the barnase ORF encoding the mature protein (Paddon and Hartley, *Gene* 40 231–239 (1986); Hartley *J. Mol. Biol.* 202 913–915 (1988) can be converted into an amber stop codon. Some other minor sequence alterations are also introduced as follows.

The sequence surrounding the amber codon is modified to facilitate identification of the correct mutant, and to change it to a sequence closer to the plant consensus sequence for end of ORF signals (sequences start at the first base of the Trp codon 35):

Normal nucleotide sequence: TGGGTGGCAT-CAAAAGGGAACCTTGCAGAC (SEQ ID NO:1)

Normal aa sequence: TrpValAlaSerLysGlyAsnLeuAlaAsp (SEQ ID NO:23)

Mutated nucleotide sequence: TAGATTGCAT-CAAAAGGGAACCTTGCAGAT (SEQ ID NO:2)

Mutated aa sequence: AmbIleAlaSerLysGlyAsnLeuAlaAsp (SEQ ID NO:24)

The mutated sequence has the ability to be translated into an active barnase protein in the presence of an amber suppressor tRNA is demonstrated in *E. coli*. When expressed in *E. coli* from the plant promoter A9, which has by chance some significant transcriptional activity in *E. coli*, the mutated barnase gene is toxic to the host cells if the barstar region is deleted. This demonstrates that the introduced amber codon is suppressed to some extent, even in the absence of known suppressor tRNA genes. This suppression could be caused by translation mistakes. It also demonstrates that the other mutations which were introduced in addition to the amber codon did not impair the activity of the barnase protein. However, mutant constructs having lost toxicity could then be isolated only from strain MC1061 which has no suptRNA genes; and in these mutants no other change than the introduced mutations were found within the coding region of the barnase gene. When reintroduced into strains MC1061 and LE392, these mutant constructs were non toxic to strain MC1061 which is not known to have suppressor tRNA genes, but still toxic to stain LE392 which has genes for tRNA supE44 (translating amber as glutamine) and supF58 (translating amber as tyrosine). It seems therefore that the spontaneous mutation selected in these constructs decreases the level of expression of the mutated barnase gene, thus making the tRNA suppressor absolutely necessary for obtaining a toxic level of barnase. The genotypes of the bacterial strains are described in "Molecular Cloning: A Laboratory Manual", Sambrook et al, Cold Spring Harbor Laboratory Press, USA, 1989, and the strains are available from public collections, as will be known to those skilled in the art.

This result demonstrates the feasibility of the system, and also suggests that a tighter system could be useful. A second amber codon is therefore engineered at the codon for Trp at position 71 of the barnase mature protein, as follows (sequence starts at 1st base of codon 70):

Normal nucleotide sequence: ACATGGCGTGAA (SEQ ID NO:3)

Normal aa sequence: ThrTrpArgGlu (SEQ ID NO:25)

Mutated nucleotide sequence: ACCTAGAGAGAA (SEQ ID NO:4)

Mutated aa sequence: ThrAmbArgGlu (SEQ ID NO:26)

The mutated genes described are expressed under control of the tapetum specific promoter A9 (WO-A-9211379) and the resultant gene is introduced into *Arabidopsis thaliana*. FIG. 1 shows the scheme used to clone the genes in the expression vector, and to transfer the construct in the plant transformation vector pBin19. Transgenic plants are obtained by Agrobacterium-mediated transformation and are fertile; they are allowed to self, and selfed seeds are collected; the seeds obtained are segregating the transgene, and plants homozygous for the transgene (plant A) are identified.

The gene coding for tRNA Trp2 (Tsai Yun Lin et al, *Plant Mol. Biol.* 18 159–160 (1992)) has been cloned from *Arabidopsis thaliana* ecotype C24, by PCR from genomic DNA, using the published sequence to design the following primers:

TW1: 5'TATCGGATCCAGGAGGAAGCAAAGCAG-TACC (SEQ ID NO:5)

TW2: 5'CCACTAGTAGATCTCCACTTCCCTTC-CTTTGTTGGA (SEQ ID NO:6)

The anticodon region is then converted by in vitro mutagenesis from CCA to CTA. The resulting mutated tRNA (SupamtRNATrp) is now able to read the amber codons as Trp codons. The suppressor tRNA gene is introduced in Arabidopsis, after being cloned in plant transformation vector pBin19 as shown schematically in FIG. 1. The T-DNA in which the suppressor tRNA gene is inserted also contains a constitutive 35S-GUS gene inactivated by a Trp to Amb mutation at codon 35. This mutated GUS is used as a reporter gene for suppressor tRNA activity in the primary transformants.

A) Numbering and Construction of Genes (FIGS. 1A and 1B)

The inactivated AMS gene (FIG. 1B):

The mutated A9-Barnase (Trp35amber) was obtained by PCR mutagenesis from the pWP127 (Paul et al, *Plant Molecular Biology*, 19:611–622 (1992)), and the mutagenised Barnase-Barstar fragment XbaI-BglII was inserted in the XbaI-BamHI sites of p1415 (described below), yielding p2013. One further round of mutagenesis from p2013 yielded p2017:A9-Barnase (Trp35amber Trp71amber). These genes were then inserted in the HindIII site of pBin19 (Bevan et al, *Nucleic Acids Research*, 22:8711–8721 (1987)) as HindIII fragments, yielding p3086 and p3088 respectively. Description of p1415:p1415 is a derivative of pWP91, where the unique EcoRV site located 3' of the CaMB transcription terminator is replaced by a HindIII site. The cassette containing the A9 promoter and the CAMV terminator can therefore be recovered from P1415 as a Hind III Fragment. pWP91 is a derivative of pJIT60 where the duplicated 35S promoter region is replaced by a 934 bases A9 promoter region from pWP75 (described in *Plant Molecular Biology*, 19, 611–622 (1992)). pWP91 therefore contains a cassette made of the A9 promoter and the CaMV terminator. pJIT60 is a derivative of pJIT30 (described in *Plant Molecular Biology*, 15, 127–136 (1990)), were the 35S promoter of pJIT30 has been duplicated.

The transactivator gene and the reporter gene (FIG. 1A):

Trp Suppressor tRNA: the PCT amplified fragment was cloned in pBlueScript SK+ (Stratagene) as shown in the figure, yielding p3071.

A BamHI-Spe insert from p3071 was reinserted in sites BglII-SpeI of p3071, yielding p3081 which contains tandem repeat of the suptRNA.

A reporter gene was built by mutagenising Trp codon 35 to create an amber codon in the GUS gene (obtained from pBI121 (Jefferson et al, *EMBO Journal* 8:3901–3907 (1987)), and then cloning the mutagenised gene (with all the regulatory sequences) in pBlue Script SK+, yielding p2010. The mutated GUS gene was then inserted as a HindIII-EcoRI fragment in the HindIII-Eco RI sites of pBin 19 yielding p3092.

The suptRNA genes were inserted next to the reporter gene: a BamHi(Klenow)-SpeI fragment from p3071 or p3081 was inserted in sites EcoRI(Klenow)-SpeI of p2010, yielding p3094 and p3096 respectively.

Figure 3:
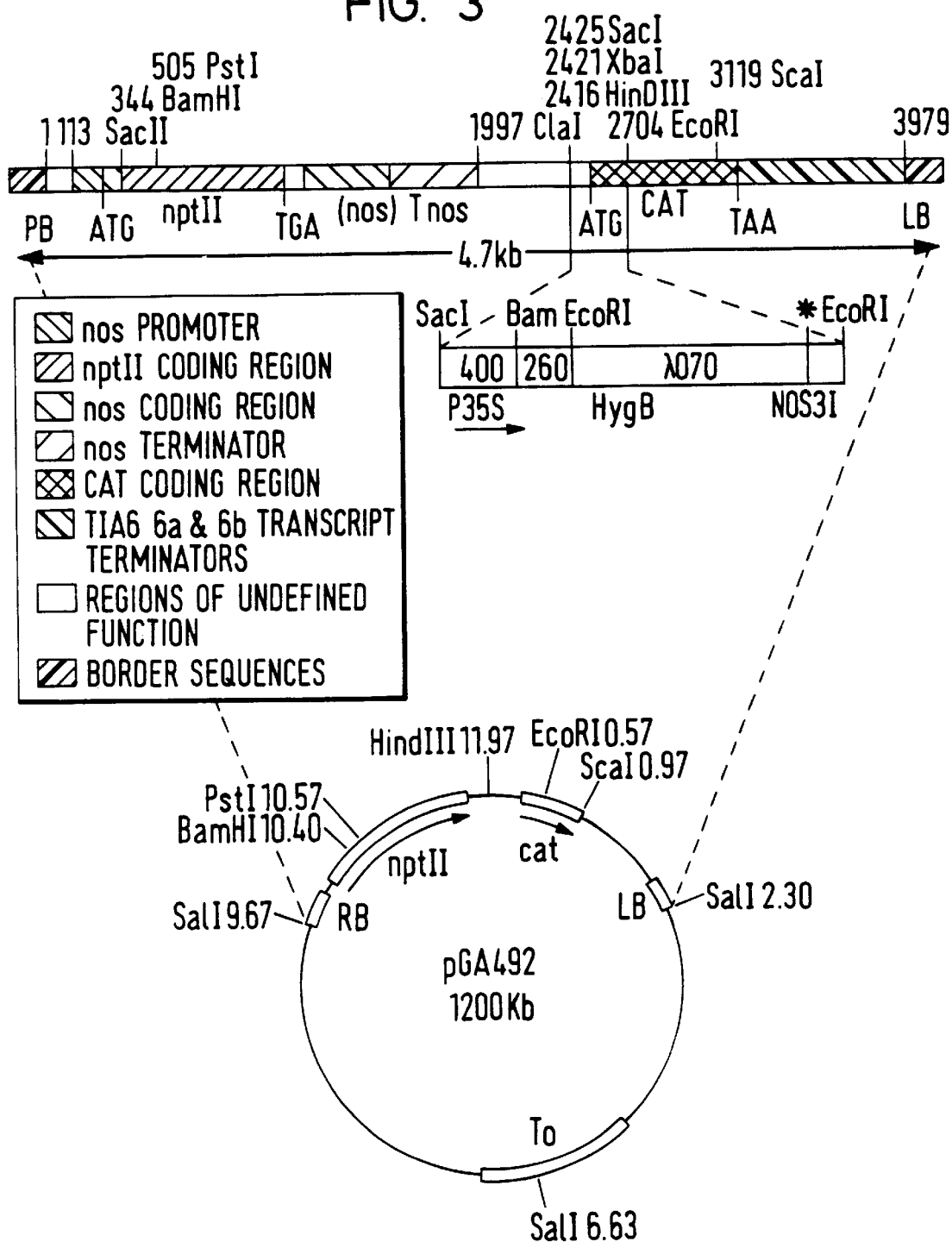
FIG. 3: is a description of pGA492 Hygro.

Transfer of this construct to binary vectors: HindIII linearised plasmids p3094 and p3096 were inserted in the HindIII site of pBin19, yielding p3108 and p3109 respectively. These plasmids contain the suptRNA gene(s) and the reporter gene. They were introduced into *Agrobacterium tumefaciens* strain AGL 1 ("AGL 1") by electroporation. The HindIII-SpeI insert from p3094 and p3096 was also inserted in the HindIII-XbaI site of another binary vector: pGA492Hygro (described below and in FIG. 3), yielding p3112 and p3113 respectively. These plasmids can be introduced in AGL1 by triparental mating.

Description of pGA492Hygro: it is a derivative of pGA492 (described in An et al, 1986, *Plant Physiology*, 81, 86–91) where a Hygromycin resistance gene made of the 35S promoter, the HygB ORF and the nos terminator has been inserted as a SacI-EcoRI fragment in the SacI-EcoRI sites of pGA492, deleting approximately 280 bases from pGA492 including the 5' end of the CAT ORF.

Combination of the AMS gene and the transactivator gene on the same T-DNA (FIG. 1B):

The HindIII fragment of p2013 containing the A9-Barnase(Trp35amber) gene was inserted in the HindIII site of p3112 and 3113 yielding p3121 and p3119 respectively. Similarly the HindIII fragment of p2017 containing the A9-Barnase (Trp35amberTrp71amber) gene was inserted in the HindIII site of p3112 and p3113, yielding p3114 and p3120 respectively. These four plasmids were introduced into AGL1 by triparental mating.

B) List of constructs introduced in plants and description

Genes are shown with their regulatory sequences (promoter and terminator); Genes are separated by "/".
p3086 A9-Barnase(Trp35amber)-CaMV
p3088 A9-Barnase(Trp35amber Trp71amber)-CaMV
p3092 35S-GUS(Trp35amber)-Nos
p3108 35S-GUS(Trp35amber)-Nos/TrpsuptRNA/ BlueScript SK+
p3109 35S-GUS(Trp35amber)-Nos/TrpsuptRNA/ TrpsuptRNA/Blue Script SK+
p3112 35S-GUS(Trp35amber)-Nos/TrpsuptRNA
p3113 35S-GUS(Trp35amber)-Nos/TrpsuptRNA/ TrpsuptRNA
p3121 A9-Barnase(Trp35amber)-CaMV/35S-GUS (Trp35amber)-Nos/TrpsuptRNA
p3119 A9-Barnase(Trp35amber)-CaMV/35S-GUS (Trp35amber)Nos/TrpsuptRNA/TrpsuptRNA
p3114 A9-Barnase(Trp35amber Trp71amber)-CaMV/35S-GUS(Trp35amber)-Nos/TrpsuptRNA
p3120 A9-Barnase(Trp35amber Trp71amber)-CaMV/35S-GUS(Trp35amber)-Nos/TrpsuptRNA/TrpsuptRNA C) Description of Plants Transgenic Arabidopsis plants were obtained by root transformation using Agrobacterium and standard methods.

The plants were evaluated for fertility and seeds harvested from fertile plants.

Plants containing the mutated GUS gene were also assayed for GUS gene expression by incubating some plant tissue (leaf and/or flower) in X-Gluc, using standard methods. GUS enzyme activity was detected by a blue staining. Most of the transformed plants had some level of GUS enzyme more noticeable in young anthers which was called background GUS("bG"). This level is probably caused by endogenous suppression of stop codons or by translation mistakes, as it could be detected also in some plants containing the mutated GUS gene only, and no exogenous suppressor tRNA. In the presence of the exogenous suppressor tRNA, a significant fraction of the plants had higher level of GUS activity: above background GUS "abG", as shown in the following table:

| Plasmids | Description of the plants: |
| --- | --- |
| p3086: | 21 plants obtained; 21 fertile. |
| P3088: | 22 plants obtained; 21 fertile; 1 sterile. |

-continued

| Plasmids | Description of the plants: |
|---|---|
| p3092: | 11 plants obtained; 11 fertile.<br>1 plant out of 10 tested shown bG.<br>No abG found. |
| p3108: | 19 plants scored for fertility; 19 fertile; sterile (flower abnormalities).<br>4 plants (1 sterile) out of 22 tested show abG. |
| p3109: | 21 plants scored for fertility; 21 fertile. .<br>10 plants out of 22 tested show abG. |
| p3120: | 4 plants obtained; 2 male sterile, 2 fertile. |

D) Plant Propagation, Genetic Analysis and Crosses.

Seeds from fertile transgenic plants (T0) have been harvested (T1 seeds), planted and homozygous T1 plants can be identified by following the segregation of the nptII (Kanamycin resistance) gene in the T2 generation.

Homozygous T1 plants containing p3086 or p3088 can then be crossed with homozygous T1 plants containing p3108 or p3109. The hybrid seeds (F1) are harvested and planted on soil. F1 families are scored for fertility. When both parents contain an efficient transgene the family has 100% sterile plants.

E) Conclusion.

The experiment demonstrates that:

The AMS gene, inactivated by 1 or 2 stop codons, has no detrimental effect on the plant fertility. It can be transactivated by suppressor tRNA in bacteria. Therefore plant A can be obtained.

Suppressor TRNA (the transactivator gene) has no effect on plant fertility but is able in a number of plants to suppress a stop codon in the GUS gene as shown by staining. the transactivator is efficient. Plant B can therefore be obtained.

The inactivated AMS gene and the suppressor TRNA gene put together by cotransformation on the same T-DNA (p3120) cause male sterility in a number of plants, showing that the presence in the same genome of the 2 genes is causing male sterility.

A male sterile plant can therefore be obtained by crossing 2 fertile plants containing an inactivated AMS gene and a transactivator respectively.

EXAMPLE 2 tRNA Mediated Suppression of a Stop Codon in an AMS Gene

The procedure of Example 1 was followed, except that codon No. 4 in the sequence of the mature barnase protein is mutated so that the Ile codon is converted to amber. The sequence surrounding the amber codon is modified as follows, for the reason given in Example 1 (sequences start at first base of codon 1 of the mature protein):

Normal nucleotide sequence: GCACAGGTTATCAAC (SEQ ID NO:7)
Normal aa sequence: AlaGlnValIleAsn (SEQ ID NO:27)
Mutated nucleotide sequence: GCACAAGTGTAGAAC (SEQ ID NO:8)
Mutated aa sequence: AlaGlnValAmbAsn (SEQ ID NO:28)

The results obtained in *E. coli* are the same as those described in Example 1. A second amber mutation is introduced at the codon for Leu at position 95 of the barnase mature protein as follows (sequences start at first base of mutagenised Leu codon 95):

Normal nucleotide sequence: CTGATTTACAAA (SEQ ID NO:9)
Normal aa sequence: LeuIleTyrLys (SEQ ID NO:29)
Mutated nucleotide sequence: TAGATTTACAAA (SEQ ID NO:10)
Mutated aa sequence: AmbIleTyrLys (SEQ ID NO:30)

Figure 2A:
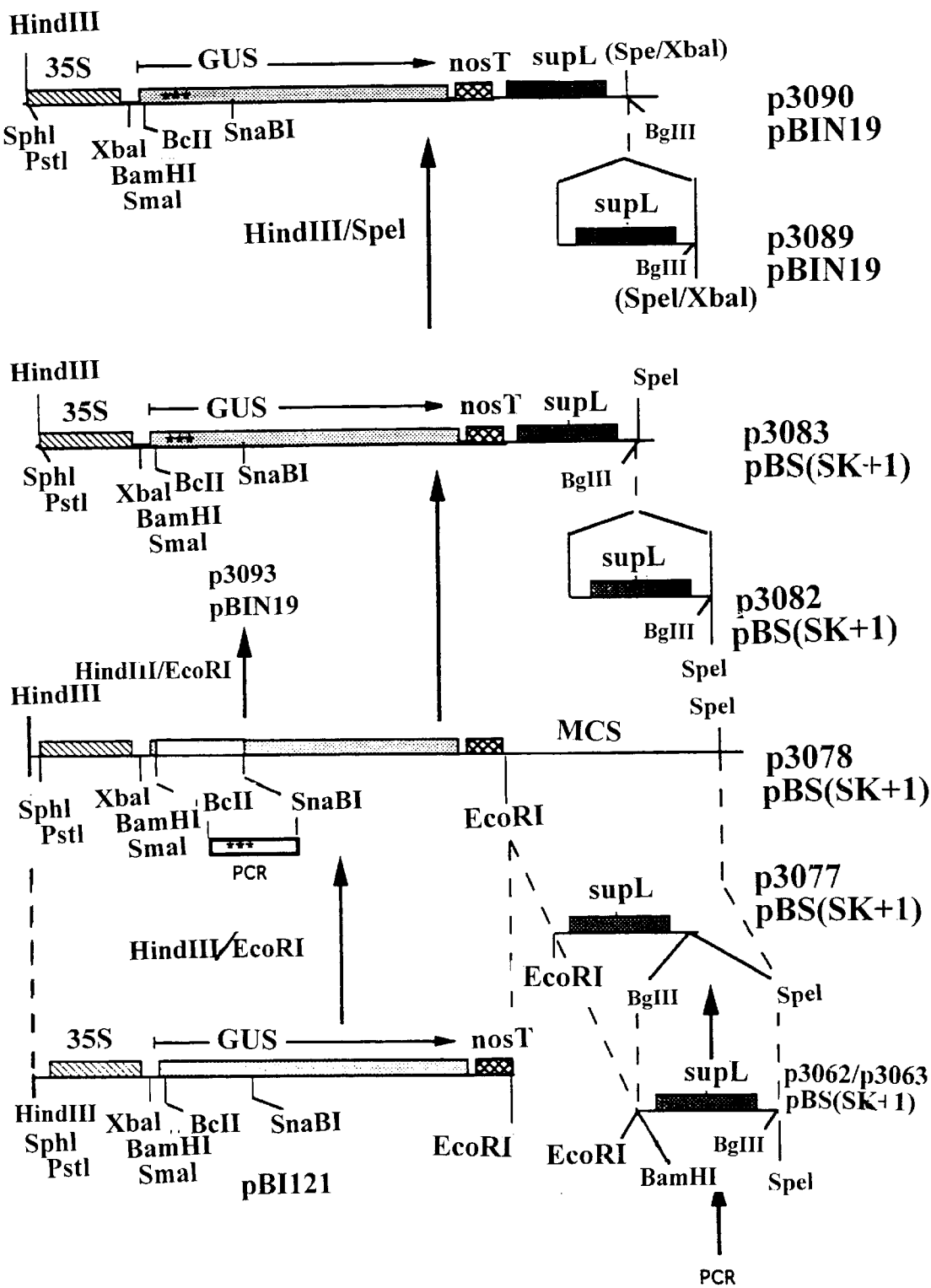
FIG. 2A: shows the scheme for cloning the transactivator and reporter genes.
Figure 2B:
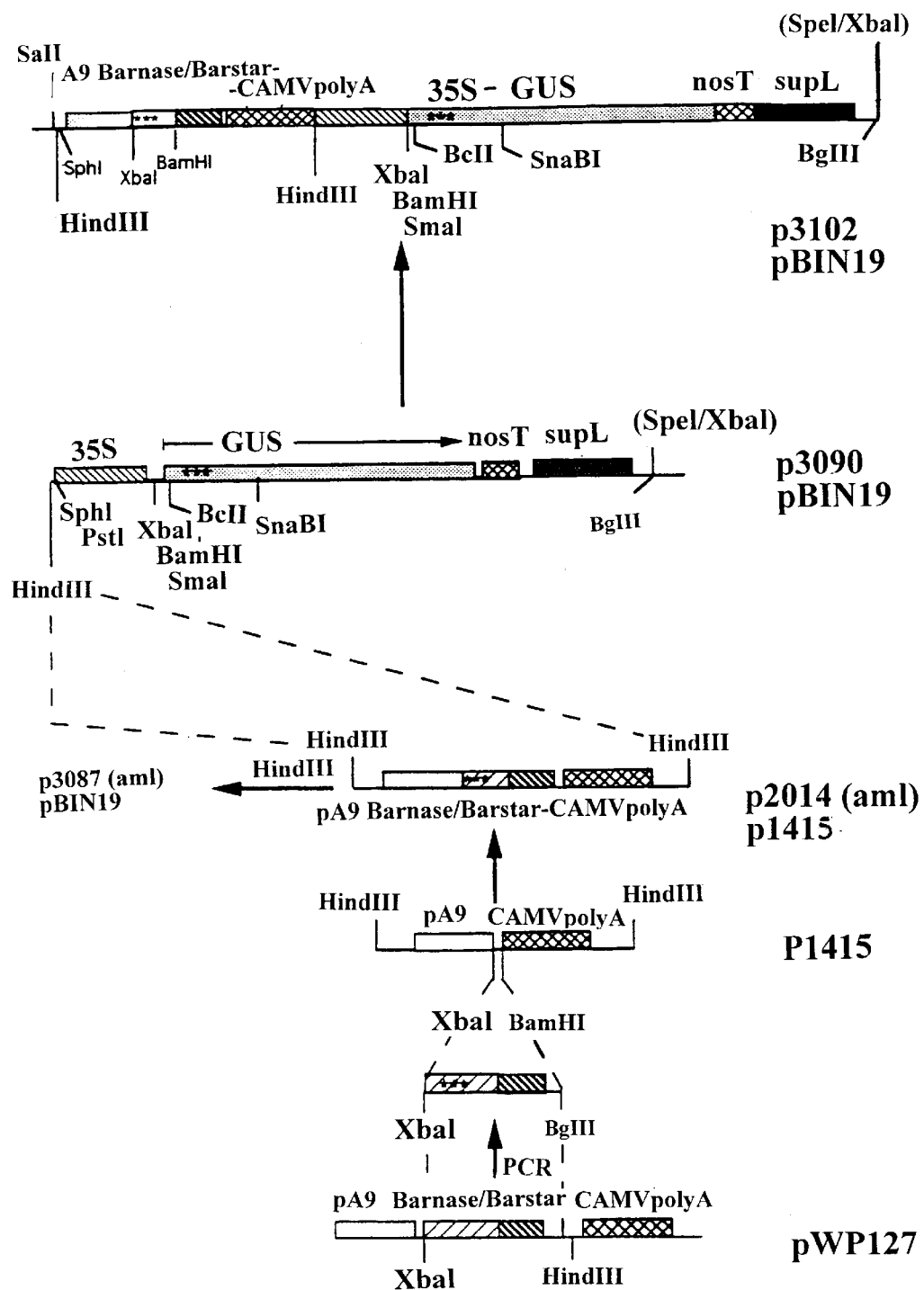
FIG. 2B: shows the scheme for cloning an AMS mutant gene (Barnase AMS)

A) Numbering and Construction of Genes (FIGS. 2A and 2B)

The inactivated AMS gene (FIG. 2B):

The mutated A9-Barnase (Ile4amber) was obtained by PCR mutagenesis from pWP127, and the mutagenised Barnase-Barstar fragment XbaI-BglII was inserted in the XbaI-BamHI sites of p1415, yielding p2014. This gene was then inserted in the HindIII site of pBIN19 as a HindIII fragment, yielding p3087.

The transactivator gene and the reporter gene (FIG. 2A): Leu Suppressor tRNA: the synthetic DNA fragment was cloned in pBlueScriptSK+ as shown in FIG. 2A, yielding p3062 and p3063 (2 identical clones).

A BamHI-BglII insert from p3063 was re-inserted in site BglII of p3063, yielding p3077 which contains a tandem repeat of the suptRNA.

A reporter gene was built by mutagenising lie codon 123 to create an amber codon in the GUS gene (obtained from pBI121), and cloning the mutagenised gene (with all the regulatory sequences) in pBlueScript SK+, yielding p3078. The mutated GUS gene was then inserted as a Hind III-EcoRI fragment in the HindIII-EcoRI sites of pBin 19 yielding p3093.

The suptRNA genes were then inserted next to the reporter gene: an EcorRI-SpeI fragment from p3062 or p3077 was inserted in sites EcoRI-SpeI of p3078, yielding p3083 and p3082 respectively.

Transfer of this construct to binary vectors: HindIII-SpeI fragments from p3083 and p3082 were inserted in the HindIII-XbaI sites of pBin19, yielding p3090 and p3089 respectively. These plasmids contain the suptRNA gene(s) and the reporter gene. They were introduced into AGL1 by electroporation.

Combination of the AMS gene and the transactivator gene on the same T-DNA (FIG. 2B):

The HindIII fragment of p2014 containing the A9-Barnase (Ile4amber) gene was inserted in the HindIII site of p3090 yielding p3102. This plasmid was introduced in AGL1 by electroporation.

B) List of Constructs Introduced in Plants and Description.

Genes are shown with their regulatory sequences (promoter and terminator); Genes are separated by "/".

p3087: A9-Barnase(Ile4amber)-CaMV
p3093: 35S-GUS(Ile123amber)-Nos
p3090: 35S-GUS(Ile123amber)-Nos/LeusuptRNA
p3089: 35S-GUS(Ile 123amber)-Nos/LeusuptRNA/LeusuptRNA
p3102: A9-Barnase(Ile4amber)-CaMV/35S-GUS(Ile123amber)-Nos/LeusuptRNA C) Description of Plants.

Transgenic plants were obtained and scored as in Example 1.

| Plasmid | Description of the plants |
|---------|---------------------------|
| p3087: | 22 plants obtained; 21 fertile; 1 sterile with flower abnormalities. |
| p3093: | 16 plants obtained; 16 fertile 8 out of 13 plants tested show bG. No abG observed. |
| p3090: | 19 plants obtained; 15 fertile; 4 sterile. 6 plants (including the 4 sterile) show abG. |
| p3089: | 8 plants obtained; 5 fertile; 2 sterile; 1 sterile with flower abnormalities. No abG observed. |
| p3102: | 8 plants obtained; 4 sterile, 4 fertile; |

The toxicity of the LeusuptRNA is unexpected as it is in contradiction with published data. It can be explained by taking into account the dual localisation (cytosolic and mitochondrial) of the bean LeutRNA chosen for the experiment: the presence of a suppressor tRNA in the mitochondria where the pool of tRNAs is limited might be deleterious for the cell. However, some plants expressing the LeusuptRNA have a normal phenotype and can be used in a cross to transactivate the inactivated AMS gene. And furthermore: the presence on the same T-DNA of the 2 genes (in p3102) increases the frequency of sterile plants showing that the transactivation is efficient.

D) Plant Propagation, Genetic Analysis and Crosses.

As in Example 1, seeds from fertile transgenic plants (T0) were harvested (T1 seeds) and planted. Heterozygous and homozygous T1 plants can be identified by following the segregation of a single nptII (Kanamycin resistance) locus in the T2 generation.

Kanamycin resistant individuals from a T1 population from a primary transformant containing p3087 were crossed as female to individuals of T1 populations from 3 primary transformants containing p3090 and expressing the tRNA gene (as shown by a RT-PCR experiment). The hybrid seeds (F1) were obtained and planted on soil.

Sterile plants in the F1 families were identified with expected frequencies:

0% if one parent is Kanamycin sensitive;

25% if both parents are heterozygous for the nptII gene;

50% if one parent is homozygous for the nptII gene;

100% if the two parents are homozygous.

E) Conclusion

The experiment demonstrates that the AMS gene, inactivated by 1 stop codon, has no effect on the plant fertility. It can be transactivated by suppressor tRNAs in bacteria. Therefore plant A can be obtained.

The suppressor tRNA has a strong, gene dosage dependent effect, on plant viability and fertility. It is nevertheless possible to obtain normal plants expressing the suppressor tRNA by screening a large population of transformants. The suppressor tRNA is efficiently transactivating a mutated reporter gene. Plant B can therefore be obtained.

When plant A was crossed to plant B, male sterile F1 plants were found in predicted ratios. This demonstrates the feasibility of generating a homogeneous population of male sterile plants from a cross of a homozygous plant A expressing the transgene A with a homozygous plant B expressing the transgene B.

EXAMPLE 3

T7 RNA Polymerase-Mediated Expression of an AMS Gene

Construction of an A9 promoter-modified T7 RNA polymerase chimeric gene. For efficient use in eukaryotic cells, the phage T7-RNA polymerase protein (T7RNP) must be modified so that it is targeted to the cell nucleus. This has been achieved in mammalian (Lieber et al, *Nucleic Acids Research* 17 8485–8493 (1989)) and plant cells (Lassner et al, *Plant Molecular Biology* 17 229–234 (1991)) by the addition of a nuclear-targeting signal from the large T-antigen of SV40 to the N-terminus of T7RNP. A similar SV40 leader-T7RNP gene fusion was constructed by Dr. Andrzej Plucienniczan in the following manner:

The T7RNP gene was isolated as an NruI, BamHI fragment from plasmid pGP1-2 (Tabor and RIchardson, *Proc. Nat'l. Acad. Sci. USA* 82 1074–1078 (1985)) and cloned between the AccI (rendered flush with Klenow) and BamHI sites of pUC19 forming the plasmid pT75. A leader sequence from the SV40 large T-antigen gene was then cloned in front of the NruI site of pT75, forming pT751.

The modified T7RNP gene of pT751 is then placed under control of the tapetum-specific A9 promoter. The XbaI-BamHI fragment containing the modified T7RNP gene is cloned between the XbaI and BamHI sites of pWP91 (described in WO-A-9211379) forming pWP180 (FIG. 2A). The A9 promoter-T7NP chimeric gene is then cloned as an XhoI fragment into the SalI site of pSCV-nos-nptII (pSCV-nos-nptII was made by cloning a nos promoter-nptII-nos terminator chimeric gene between the EcoRV and EcoRI sites of pSCV1 (see Firek et al, *Plant Molecular Biology*, 22: 129–142 (1993) for information on pSCV1). The resulting plasmid (pWP180-SCV) is then transformed into plants and bred to homozygosity (plant A).

Construction of a T7 promoter PR-glucanase chimeric gene.

An EcoRI, XhoI fragment containing the A9 untranslated 5' leader sequence and the 5' region of the PR glucanase gene from pDW80PR (Worrall et al, *The Plant Cell* 4 759–771 (1992)) is cloned between the EcoRI, SalI sites of the vector pTZ18 (Pharmacia Ltd) forming pWP178. Transcription by T7-RNA polymerase from the T7 promoter produces RNA that is uncapped and thus may be unstable or poorly translated in eukaryotes. Addition of a 5' leader sequence that allows cap-independent translation, such as the Tobacco Etch viral leader (TEV) (Carrington and Freed, *Journal of Virology*, 64: 1590–1597 (199)), markedly increases translation of protein from RNA transcribed by T7-RNA polymerase (Tuttle et al, *4th International Congress of Plant Molecular Biology*, Abstracts p478 (1994)). The TEV leader sequence is therefore cloned as an EcoRI-NcoI fragment between the EcoRI and NcoI sites of pWP178, thus removing the A9-leader, forming pWP178-TEV.

A modified T7 primer:

5' GGGGCTCGAGTTAATACGACTCACTATAGGG 3' (SEQ ID NO:11) (an XhoI site added 5' to the T7 promoter)

and the M13 20' primer:

5' CGTTGTAAAACGACGGCCAG 3' (SEQ ID NO:12) (primes outside the polylinker of pTZ18)

are then used in a polymerase chain reaction to obtain a T7 promoter TEV leader-PRgluc' fragment that is cloned into pBluescript II KS-(Stratagene Ltd) as an XhoI, HindIII fragment, forming pWP188-TEV. The KpnI-NcoI fragment of pWP188-TEV is then used to replace the KpnI-NcoI A9 promoter-leader fragment of pDW80PR, forming pWP222.

Primers:

5' CCGCATGCGATCCGGCTGCTAACAAAGCC 3' (SEQ ID NO:13) and

5' GGATATCAGATCTCGATCCGGATATAGTTCC 3' (SEQ ID NO:14)

are used in polymerase chain reaction with plasmid ET-21-a (Novagen) as template and the resulting T7 terminator sequence is cloned as a SphI, EcoRV fragment between the SphI and EcoRV sites of pWP222, forming pWP224. The T7 promoter TEV-PRgluc chimeric gene is then cloned as a partial XhoI fragment into the SalI site of the binary vector. SCV nos-nptII, forming pWP224-SCV, and transformed into plants and bred to homozygosity (plant B(PRgluc)).

Construction of a 17 promoter-TEV-Barnase chimeric gene.

The NcoI, SphI PR-Gluc and CaMV polyadenylation sequences of pWP224 were replaced with the NcoI SphI Barnase and CaMV polyadenylation sequences of pWP128 (Paul et al, *Plant Molecular Biology*, 19: 611–622 (1992)), forming pWP226. This chimeric T7 promoter-TEV-Barnase gene was cloned as an XhoI fragment into the SalI-cut pSCB-nos-nptII, forming pWP226-SCV. The T7 promoter-TEV-Barnase gene could not be transferred intact into tobacco plants, indicating that, as observed previously in mammalian cells (Leiber et al, *Methods in Enymology*, 217: 47–66 (1993)), the T7 promoter is recognised, albeit at low efficiency, by a eukaryotic RNA polymerase. Since Barnase is highly cytotoxic to all plant cell types (unlike Pr-gluc (Worrall et al, *The Plant Cell*, 4: 759–771 (1992)), any low level "constitutive" expression of Barnase would prevent regeneration of transformed plants. Mutations of the T7 promoter sequence can significantly reduce non-specific expression from the T7 promoter, whilst still allowing recognition by T7 RNA polymerase (Leiber et al, *Methods in Enzymology*, 217: 47–66 (1993)). Thus the T7 promoter of pWP226 is replaced with such a mutated promoter.

A mutated T7 primer:

5' GGGCTCGAGTTAATTCGACTCACTATACGG 3' (SEQ ID NO:15) (A nXhoI site added 5' to the T7 promoter)

and the M13 20' primer:

5' CGTTGTAAAACGACGGCCAG 3' (SEQ ID NO:16) (primes outside the polylinker of pTZ18)

are then used in a polymerase chain reaction to obtain a mutant T7 promoter TEV leader-Prgluc' fragment from pWP178-TEV, that is then cloned into pBluescript II KS-(Stratagene Ltd) as an XhoI, HindIII fragment forming pWP188-T7mut. The KpnI-NcoI fragment of pWP188-T7mut is then used to replace the KpnI-NcoI fragment of pWP226 forming pWP226-T7mut. The T7-mut promoter TEV-Barnase chimeric gene is then cloned as an XhoI fragment into the SalI site of the binary vector SCV nos-nptII, forming pWP226-T7mut-SCV, and transformed into plants and bred to homozygosity (plant B (Bamase)).

In the progeny (plant AB(PRgluc) or plant AB(Barnase)), the T7RNP is present in the tapetum of these plants and promotes expression in the tapetum of either the T7-TEV-PRgluc or T7-mut-TEV-Barnase genes therefore causing male sterility. The use of the system in a hybrid seed production scheme is similar to the one described in Example 1 above.

EXAMPLE 4

T7 RNA Polymerase-Mediated Expression of GUS in Seeds

To demonstrate the utility of T7 RNA polymerase-mediated expression of proteins or RNAs in seeds or in the other parts of the hybrid plant, expression of GUS protein from such a system in seeds is described below.

Construction of a 35S CaMV promoter-modified T7 RNA polymerase chimeric gene.

For efficient use in eukaryotic cells, the phage T7-RNA polymerase protein (T7RNP) must be modified so that it is targeted to the cell nucleus. This has been achieved in mammalian (Leiber et al, *Nucleic Acids Research*, 17: 8485–8493 (1989)) and plant cells (Lassner et al, *Plant Molecular Biology*, 17: 229–234 (1991)) by the addition of a nuclear-targeting signal from the large T-antigen of SV40 to the N-terminus of the T7RNP. A similar SV40 leader-T7RNP gene fusion was constructed by Dr Andrzej Pluci-enniczan in the following manner:

The T7RNP gene was isolated as an NruI, BamHI fragment from plasmid pGP1-2 (Tabor and RIchardson, *Proc. Natl. Acad. Sci. USA*, 82: 1074–1078 (1985)) and cloned between the AccI (rendered flush with Klenow) and BamHI sites of pUC19 forming the plasmid pT75. A leader sequence from the SV40 large T-antigen gene was then cloned in front of the NruI site of pT75, forming pT751.

The modified T7RNP gene of pT751 is then placed under control of a double 35S CaMV promoter. The XbaI-BamHI fragment containing the modified T7RNP gene is cloned between the XbaI and BamHI sites of pWP90, forming pWP179 (FIG. 2A). pWP90 is identical to pWP91 (described in WO-A-9211379) except that the KpnI, XbaI A9 promoter fragment of pWP91 is replaced by a KpnI, XbaI double 35S promoter from pJIT 60 (described in WO-A-9211379). The 35S CaMV promoter-T7RNP chimeric gene is then cloned as an SstI,XhoI fragment into the SstI, SalI sites of pBin19. The resulting plasmid (pWP179-Bin) is then transformed into plants and bred to homozygosity (plant A).

Construction of a T7 promoter-TEV-GUS chimeric gene.

An EcoRI,EcoRV fragment containing the Tobacco Etch Virus (TEV) leader sequence and the 5' region of β-Glucuronidase (GUS) from pRTL2GUS (Carrington and Freed, *Journal of Virology*, 64: 1590–1597 (1990)) is cloned between the EcoRI,SmaI sites of the vector pTZ18 (Pharmacia Ltd) forming pGUS1 (cap-independent leader sequences such as TEV (Carrington and Freed, *Journal of Virology*, 64: 1590–1597 (1990)) have been shown to improve significantly the stability and translatability of RNA transcripts made by T7 RNA polymerase in plant protoplasts (Tuttle et al, 4*th Internation Congress of Plant Molecular Biology*, Abstracts p478 (1994)). A modified T7 primer:

5' GGGGCTCGAGTTAATACGACTCACTATAGGG 3' (SEQ ID NO:17) (An XhoI site added 5' to the T7 promoter)

and the M13 20' primer:

5' CGTTGTAAAACGACGGCCAG 3' (SEQ ID NO:18) (primes outside the polylinker of pTZ18)

are then used in a polymerase chain reaction to obtain a T7 promoter TEV leader-GUS' fragment that is cloned into pBluescript II KS-(Stratagene Ltd) as an XhaoI, HindIII fragment forming pGUS2. The KpnI-NcoI fragment of pGUS2 is then used to replace the KpnI-NcoI A9 promoter of pWP91 (described in WO-A-9211379) forming pGUS3.

Primers:

5' CCGCATGCGATCCGGCTGCTAACAAAGCC 3' (SEQ ID NO:19) and

5' GGATATCAGATCTCGATCCGGATATAGTTCC 3' (SEQ ID NO:20)

are used in polymerase chain reaction with plasmid ET21a (Novagen) as template and the resulting T7 terminator sequence is cloned as a SphI, EcoRV fragment between the SphI and EcoRV sites of pGUS3 forming pGUS4. The NcoI, SphI fragment from pRTL2GUS, containing the GUS and CaMV polyadenylation sequences, are then cloned between the NcoI and SphI sites of pGUS4 forming pWP225. The T7 promoter TEV-GUS chimeric gene is then cloned as an XhoI fragment into the SalI site of the binary vector SCV nos-nptII (pSCV-nos-nptII was made by cloning a nos promoter-nptII nos terminator chimeric gene between the EcoRV and EcoRI sites of pSCV1 (see Firek et al, *Plant Molecular Biology*, 22: 129–142 (1993) for information on pSCV1), forming pWP225-SCV, and transformed into plants and bred to homozygosity (plant B).

In the developing seeds resulting from a cross of plant A to B, T7RNP expression results in the transcription of the T7-TEV-GUS gene and GUS protein accumulation in all cells and tissues where the 35S promoter is active. This demonstrates that expression of a heterozygous protein in a seed-specific manner can be obtained.

EXAMPLE 5

Activation of an AMS Gene by Specific Splicing

An AMS gene, such as A9-barnase or A3-glucanase, is built containing an artificial intron which prevents translation of the gene. An appropriate group I intron derived from a mitochondrial rRNA gene from *Neurospora crassa* is described in Guo et al, *The Journal of Biological Chemistry* 266 1809–1819 (1991). This intron is not able to self-splice and needs a specific protein helper for splicing. In plants, the intron should not be spliced. Plant A (the first line) contains such an AMS gene, is fertile and bred to homozygosity. Plant B (the second line) contains an engineered gene encoding the protein needed for splicing: the CYT-18 protein from *Neurospora crassa*; the ORF is manipulated so that the protein will be targeted to the nucleus, and if necessary so that its other activity (tyrosyl-tRNA synthetase) is abolished (Mohr et al, *Cell* 69 483–494 (1992)). This gene in itself has no effect on the plant containing it; plant B is fertile and bred to homozygosity. Cross between A and B is performed as described above and the seeds obtained give sterile plants. These can be used in a hybrid seed production scheme as described in Example 1 above. Other intron/helper protein pairs could be used.

EXAMPLE 6

Activation of a Bicistronic AMS Gene by Protein VI of CaMV

An AMS ORF (such as Barnase or PR glucanase as described above) is inserted in 3' of (after the Stop codon of) a first ORF (Zijlstra and Hohn, *The Plant Cell* 4 1471–1484 (1992); they describe the use of ORF VII from CaMV, but recommend the use of the ORF for NPTII, such that the AMS ORF is present on the same mRNA as the first ORF. Because only the first ORF is translated in plant mRNA, the AMS ORF is not translated. The plant containing this bicistronic gene (plant A) is fertile and bred to homozygosity.

An activator of the translation of the AMS ORF in gene A is the product of ORF VI of CaMV, (Zijlstra and Hohn 1992, ibid). Gene B is built by placing ORF VI of CaMV under control of an appropriate promoter such as A9. In plants (plant B), this gene has no effect and the plant is bred to homozygosity.

In plant AB resulting from the cross between A and B, the product of gene VI activates translation of the AMS ORF present on the bicistronic mRNA, and the resulting protein causes sterility.

The system is then used as described in Example 1 above to generate a homogeneous population of male sterile plants, used to produce hybrid seeds.

EXAMPLE 7

Transcription Transactivation

Gene A is an AMS gene under control of a specific promoter which is not active in the absence of its cognate transacting factor.

Gene B is a gene coding for the transacting transcription activator, expressed in the appropriate tissue.

EXAMPLE 8

RIbozyme Inactivation of a Gene Necessary for Male Fertility

Dominant male sterility can be obtained by inhibiting expression of an endogenous gene needed for male fertility. This gene suppression can be done using antisense RNA technology or using ribozyme RNA technology. The latter can be deployed so that a binary system causing sterility can be designed and this is described below. The target gene to be suppressed can be identified for example by analysis of male sterile mutants. There are many examples of potential target genes (such as gene ms2 of Arabidopsis, Aarts et al., *Nature* 363 715–717 (1993)). Target genes from plants of interest can be cloned from other plants, using knowledge derived from the Arabidopsis gene or genes and using standard technologies (such as the use of heterologous probes, antibodies and PCR reactions using degenerate primers). A suitable target gene is called in this description "ms" and its gene product called "MS".

In plant A is introduced a T-DNA containing a ribozyme directed against a site (called site 1) in gene ms, and a mutated version of gene ms (called ms1*-2) where the ribozyme cleavage site has been mutated, and a different cleavage site created (site 2) without destroying the MS protein function. In this plant endogenous gene ms expression is destroyed by the ribozyme, but this is complemented by expression of gene ms1*-2 which is resistant to ribozyme cleavage.

Plant A contains MS, and is therefore fertile, this fertility being conferred by the expression of ms1*-2, an allele of gene ms. It is bred to homozygosity.

Plant B expresses a ribozyme directed against site 2 of gene ms1*-2. This site is not present in gene ms, and therefore plant B has normal MS activity. It is fertile and bred to homozygosity.

Plant AB will lack MS activity because the ribozyme from plant A will inactivate gene ms and the ribozyme from plant B will inactivate gene ms1*-2. This plant will be sterile, and can be used to produce hybrid seeds as described in Example 1 above.

If restoration is needed, a new allele of gene ms (ms1*-2*) can be made where site 2 would be mutated to be resistant to ribozyme cleavage, without destroying MS protein function.

For a given gene ms, such as ms2, characterised by the phenotype of a ms deficient mutant, and where sequence of the mRNA is known, the information needed to build the system is available.

As an example of this approach, a test system is the restoration of fertility of an *Arabidopsis thaliana* ms2 male sterile line (Aarts et al, *Nature*, 363: 715–717 (1993)), using an ms2 cDNA (C103) isolated from *Brassica napus* (Hodge et al, *The Plant Journal*, 2: 257–260 (1992)). The tapetum-specific A9 promoter can be used to drive expression of the *Brassica napus* ms2 cDNA (C103). This construct will produce ms2 protein in the tapetum and thereby restore fertility to plants in which the native ms2 gene, RNA or protein has been disrupted.

Construction of a chimeric gene containing the tapetum-specific A9 promoter linked to the sense orientation of the C103 cDNA and transformation into ms2 *Arabidopsis thaliana*.

Figure 4:
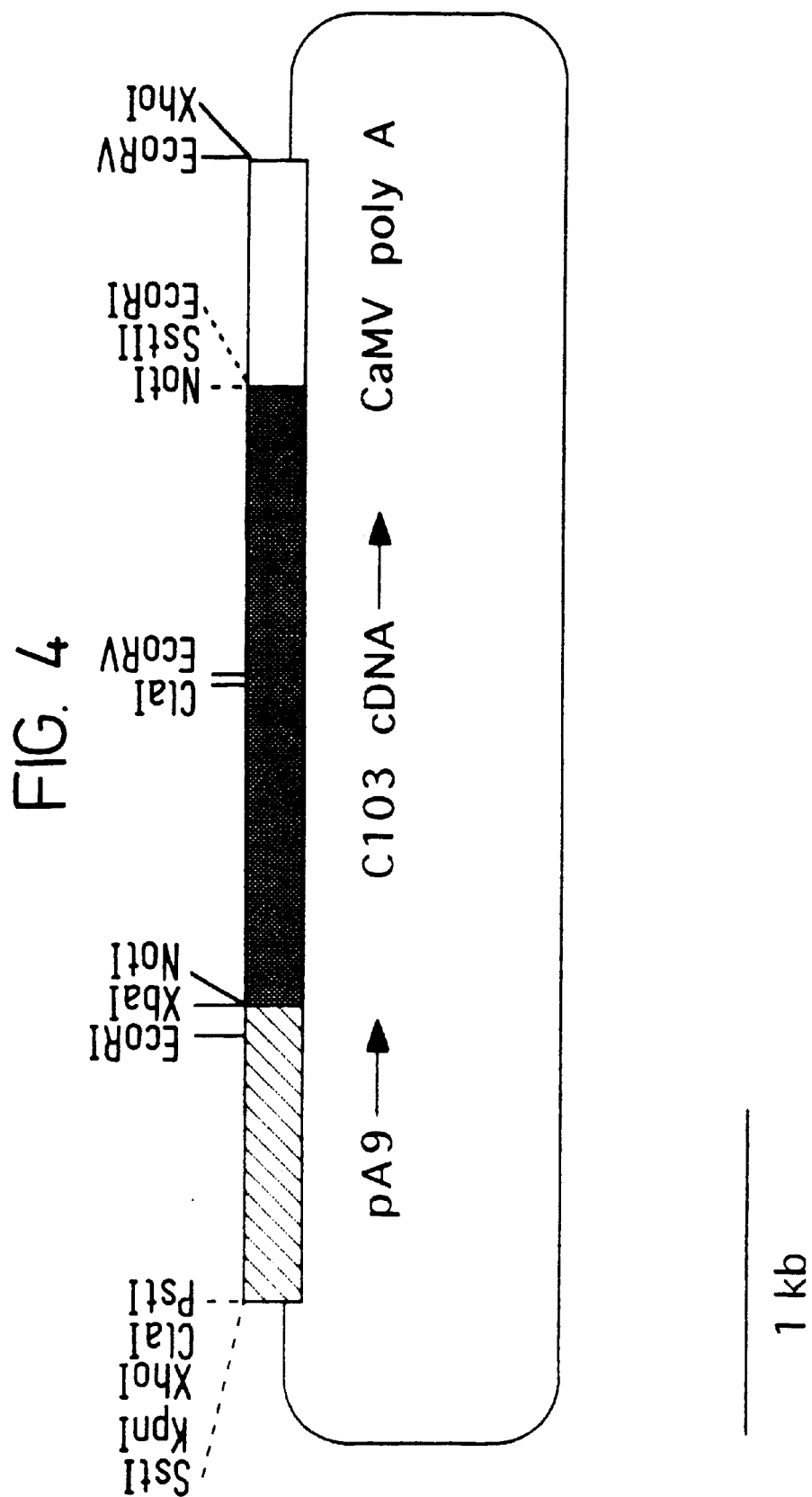
FIG. 4: shows the structure of the A9 promoter-C103 chimeric gene excised from pWP80 in Example 7.

The anther-specific cDNA C103 was cloned into the EcoRI site of Lambda ZapII (Stratagene) by the addition of EcoRI/NotI linkers (Hodge et al, *The Plant Journal*, 2, 257–260 (1992)). The cDNA can be excised as a NotI fragment since there are no internal NotI sites. The cDNA is then cloned into NotI-cut pWP80 (UK Patent No 9028060.3) in the sense orientation. The chimeric gene is then excised from the pWP80 derivative with XhoI and is cloned into SaI-cut pBin19 (Bevan et al, *Nucleic Acids Research*, 22, 8711–8721 (1984) (FIG. 4)).

The pBin19 derivatives are transformed into the plant species of interest. Plants which are male sterile due to disruption of native ms2 gene function are male fertile upon transformation or crossing in of this restorer gene.

Since sequences of the *A. thaliana* and *B. napus* ms2 are not identical (89% identity between their coding regions, FIG. 5), specific ribozymes can be designed that cleave only the *A. thaliana* or only the *B. napus* ms2 mRNA. these can be used in the binary system scheme as outlined previously.

EXAMPLE 9

Sterility Induction by Repressing the Inactivator of an Active AMS Gene

In line A, the AMS gene is co-expressed with an inactivator of the AMS gene producing fertile plants. Line A is then crossed to Line B that expresses a repressor of the inactivator such that the hybrid AB is male-sterile.

An example of such a system is Barnase as the AMS gene, Barstar as the inactivator and anti-Barstar as the repressor. Expression of Barstar from the tapetum-specific TA29 promoter restores fertility to sterile TA29-Barnase *Brassica napus* plants (Mariani et al, *Nature*, 357: 384–387 (1992)). Thus co-expression of Barnase and Barstar from the same tapetum-specific promoter, for example A3 or A9, will produce male-fertile plants. Barnase and Barstar expression can also be driven from different promoters providing that the temporal and spatial pattern of expression of Barnase is encompassed by the expression of Barstar. Thus the tapetum-specific promoters A3 and A9 which have similar patterns of expression (UK Patent Application No 9028060.3) can be used to drive Barnase and Barstar in the combinations A3-Barnase+A9-Barstar and A9-Barnase+A3-Barstar. Similar promoter combinations may be advantageous either to provide Barstar prior to Barnase expression in the cell or to produce more Barstar than Barnase in the cell.

A) Numbering and Construction of Genes

The active AMS gene: A3-Barnase (pWP131 (see UK Patent Application No 9028060.3))

The inactivator of the AMS gene combined with the AMS gene:

The inactivator gene is A9-Barstar: this was built by inserting the Barstar ORF as a BamHI-BgIII fragment, produced by PCR from pWP127, in the BamHI site of p1415, in the sense orientation, yielding p3072. The SphI fragment from p3072 containing the A9-Barstar gene was inserted in the sphI site of pWP131 which contains the A3-Barnase-CaMV gene, yielding p2021. The salI-EcoRV fragment of p2021 which contains the 2 genes was then inserted in the SalI-SmaI sites of pBin 19 yielding p3118. This plasmid contains the 2 genes in the same T-DNA. It was introduced in AGLI by electroporation.

The repressor gene of the inactivator:

The same Barstar ORF BamHI-BgIII fragment, produced by PCR from pWP127 as described above, was inserted in the BamHI site of p1415 in the antisense orientation yielding p3073. The HindIII fragment of p3073 containing the A9-antiBarstar gene was inserted in the HindIII site of pBin19 yielding p3076. This plasmid was introduced in Agrobacterium by electroporation.

B) List of Constructs Introduced in Plants and Description

Genes are shown with their regulatory sequences (promoter and terminator); Genes are separated by "/".

p3118 A3-Barnase-CaMV/A9-Barstar-CaMV p3076 A9-antiBarstar-CaMV

C) Description of Plants

Transgenic plants were obtained and scored as in Example 1.

| Plasmid | Description of the plants |
|---|---|
| p3076: | 14 plants obtained; 13 fertile; 1 sterile with abnormal flowers. |

D) Plant Propagation, Genetic Analysis and Crosses

As in Example 1, seeds from fertile transgenic plants (T0) are harvested (T1 seeds), planted and heterozygous and homozygous T1 plants can be identified by following the segregation of the marker gene in the T2 generation.

Homozygous plants from various primary transformants containing p3118 are crossed to homozygous plants from various transformants containing 3076. The hybrid seeds (F1) are planted and F1 plants are scored for fertility. When the 2 transgenes are efficient the F1 plants are sterile.

E) Conclusion

Given the known temporal and spatial activities of the A3 and the A9 promoter(Scott et al, *Plant Molecular Biology*, 17:195–207(1991) plant A can be obtained. A gene able to reduce or suppress expression of the restorer gene has no effect on fertility. Plant B can be obtained.

EXAMPLE 10 fad2 mutants of *Arabidopsis thaliana* which are deficient in ER 18:1 desaturase are inhibited in germination at low temperatures (M F Miquel and J A Browse, *Plant Physiology*, 106: 421–427). This strongly suggests that driving seed specific antisense to this gene, giving rise to high oleic acid in the seed oil as described in WO 93/11245, would result in inhibition of seed germination of high oleate oilseed rape. Indeed, the authors conclude that the production of commercially viable high oleate (rape) oil "may not be possible". High oleic acid rape is a desired product for industrial feed stock.

Using the binary system as described above in Example 3 can alleviate this problem. Thus, lines A and B are created. The A line carries the phage T7 RNA polymerase protein (T7RNP) linked to a seed specific promoter such as the napin promoter. Any suitable promoter may be used, including a seed specific promoter which may be preferred over 35S since expression in the seed is higher. The B line carries the T7 promoter linked to the desaturase gene in the antisense orientation (this replaces GUS from Example 3). In the developing seeds resulting from the cross A to B, T7RNP expression results in the transcription of the T7-TEV-antidesaturase gene. Both A and B can be multiplied separately without the gene being expressed. The A line is chosen to be or subsequently rendered male sterile (cytoplasmic male sterility is commonly used in the female parents of oilseed rape) or otherwise incapable of selfing, and the B line to be a suitable pollinator, thereby ensuring that seed collected on the hybrid carries the two components. There may be further refinements of the production system. (Note, however, that the ratio of A:B is certainly not 1:1, and may be around 95:5, thereby alleviating concerns about dilution of the AB seed. Alternatively, herbicide resistance may be added to the A line to allow elimination of contaminating B plants after pollination has taken place.) Only when the lines carrying the two components are crossed would expression of antisense ER18:1 desaturase occur.

In the developing seeds resulting from the cross A to B, T7RNP expression results in the transcription of the T7-antidesaturase gene. The desaturase enzyme level is thereby down regulated in tissues where the napin promoter is active, and seed resulting from the cross are high in oleic acid and thus suitable for industrial processing. Since these seeds are not intended for field planting, any gene expression during germination is no longer a problem. Seed from plants carrying the components can be germinated and therefore increased as normal.

As well as solving this particular problem, the binary system may be used in this way to express other enzymes involved in fatty acid synthesis, or in other processes occurring in the seed of crop plants, thereby ensuring security of production by having the target enzyme expressed only in the final product produced by the seed producer.

What is claimed is:

1. A method for producing a male sterile plant, the method comprising crossing a first plant which is not male sterile with a second plant which is not male sterile, wherein the first plant contains:
   (i) an expressed gene giving rise to the male sterile phenotypic trait, wherein the expressed gene encodes a ribonuclease driven by a male organ-specific promoter; and
   (ii) an expressed restorer gene which restores male fertility, wherein the expressed restorer gene encodes a ribonuclease inhibitor protein; and wherein the second plant contains:
      a repressor gene which represses the activity of the restorer gene, wherein the repressor gene is a gene encoding an antisense molecule to the restorer gene; and
      wherein the male sterility does not result from the action of a transactivator polypeptide on a target sequence.

2. A method for producing a male sterile plant, the method comprising crossing a first plant which is not male sterile with a second plant which in not male sterile, wherein the first plant contains:
   (i) an expressed gene giving rise to the male sterile phenotypic trait, wherein the expressed gene encodes the ribonuclease barnase driven by a male reproductive organ specific promoter; and
   (ii) an expressed restorer gene which restores male fertility, wherein the expr essed restorer gene encodes the Barstar toxin inhibitor; and wherein the second plant contains a repressor gene which represses the activity of the restorer gene,
      wherein the repressor gene is a gene encoding an antisense molecule to the Barstar gene, and
      wherein the male sterility does not result form the action of a transactivator polypeptide on a target sequence.

3. A male sterile plant obtained by the method of claim 1.

4. A male sterile plant obtained by the method of claim 2.

5. A method for producing a male sterile plant, the method comprising crossing a first plant which is not male sterile with a second plant which is not male sterile,
   wherein at least one of the first plant and second plant is transgenic;
   wherein the first plant comprises either
      A) (i) a male sterility gene coding for a protein which causes the male sterile phenotypic trait, and (ii) an expressed restorer gene giving rise to a protein which restores male fertility, or
      B) a male sterility gene coding for a protein which causes the male sterile phenotypic trait wherein the gene is inactivated by one or more stop codons in the gene;
   wherein the second plant comprises, respective to the first plant, either
      A) a repressor gene coding for an antisense RNA molecule that inactivates the restorer gene of the first plant, or
      B) a gene encoding one or more suppressor tRNAs which suppress the stop codon(s) in the male sterility gene of the first plant; and
   wherein the male sterility does not result from the action of a transactivator polypeptide on a target nucleotide sequence.

6. The method of claim 5, wherein the male sterility gene of the first plant is driven by a male reproductive organ-specific promoter.

7. The method of claim 5, wherein the male sterility gene encodes a ribonuclease.

8. The method of claim 5, wherein the male sterility gene encodes the ribonuclease Barnase.

9. The method of claim 5, wherein the protein causing the male sterile phenotypic trait is a ribonuclease;

wherein the expressed restorer gene which restores male fertility encodes a ribonuclease inhibitor protein; and wherein the repressor gene of the second plant encodes an antisense RNA molecule which inactivates the restorer gene of the first plant.

10. The method of claim 9, wherein the protein causing the male sterile phenotypic trait is the ribonuclease Barnase;

wherein the expressed restorer gene which restores male fertility encodes the Barstar toxin inhibitor; and wherein the repressor gene is a gene encoding an antisense RNA molecule which inactivates the Barstar gene.

11. A male sterile plant obtained by the method of claim 5 and comprising the repressor gene or the gene encoding the suppressor tRNA.

12. A male sterile plant obtained by the method of claim 6 and comprising the repressor gene or the gene encoding the suppressor tRNA.

13. A male sterile plant obtained by the method of claim 7 and comprising the repressor gene or the gene encoding the suppressor tRNA.

14. A male sterile plant obtained by the method of claim 8 and comprising the repressor gene or the gene encoding the suppressor tRNA.

15. A male sterile plant obtained by the method of claim 9 and comprising the repressor gene or the gene encoding the suppressor tRNA.

16. A male sterile plant obtained by the method of claim 10 and comprising the repressor gene or the gene encoding the suppressor tRNA.

17. Propagating material of the plant claimed in any one of claims 11–16.

18. The propagating material of claim 17 which is seed.

19. A hybrid plant obtained by crossing a male plant with the male sterile plant of claim 5.

20. A hybrid plant obtained by crossing a male plant with the male sterile plant of claim 16.

* * * * *

```
                         SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
         (A) LENGTH: 30 base pairs
         (B) TYPE: nucleic acid
         (C) STRANDEDNESS: single
         (D) TOPOLOGY: unknown (ii) MOLECULE TYPE: DNA (genomic)

(iii) HYPOTHETICAL: NO (iii) ANTI-SENSE: NO (xi) SEQUENCE DESCRIPTION: SEQ ID NO: 1:

TGGGTGGCAT CAAAAGGGAA CCTTGCAGAC                                        30

(2) INFORMATION FOR SEQ ID NO: 2:

(i) SEQUENCE CHARACTERISTICS:
         (A) LENGTH: 30 base pairs
         (B) TYPE: nucleic acid
         (C) STRANDEDNESS: single
         (D) TOPOLOGY: unknown (ii) MOLECULE TYPE: DNA (genomic)

(xi) SEQUENCE DESCRIPTION: SEQ ID NO: 2:

TAGATTGCAT CAAAAGGGAA CCTTGCAGAT                                        30

(2) INFORMATION FOR SEQ ID NO: 3:

(i) SEQUENCE CHARACTERISTICS:
         (A) LENGTH: 12 base pairs
         (B) TYPE: nucleic acid
         (C) STRANDEDNESS: single
         (D) TOPOLOGY: unknown (ii) MOLECULE TYPE: DNA (genomic)
```

(xi) SEQUENCE DESCRIPTION: SEQ ID NO: 3:

ACATGGCGTG AA                                                                                         12

(2) INFORMATION FOR SEQ ID NO: 4:

(i) SEQUENCE CHARACTERISTICS:
        (A) LENGTH: 12 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 4:

ACCTAGAGAG AA                                                                                         12

(2) INFORMATION FOR SEQ ID NO: 5:

(i) SEQUENCE CHARACTERISTICS:
        (A) LENGTH: 31 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 5:

TATCGGATCC AGGAGGAAGC AAAGCAGTAC C                                                                    31

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 6:

CCACTAGTAG ATCTCCACTT CCCTTCCTTT GTTGGA                                                               36

(2) INFORMATION FOR SEQ ID NO: 7:

(i) SEQUENCE CHARACTERISTICS:
        (A) LENGTH: 15 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 7:

GCACAGGTTA TCAAC                                                                                      15

(2) INFORMATION FOR SEQ ID NO: 8:

(i) SEQUENCE CHARACTERISTICS:
        (A) LENGTH: 15 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 8:

GCACAAGTGT AGAAC                                                                                      15

(2) INFORMATION FOR SEQ ID NO: 9:

(i) SEQUENCE CHARACTERISTICS:
        (A) LENGTH: 12 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 9:

CTGATTTACA AA                                      12

(2) INFORMATION FOR SEQ ID NO: 10:

(i) SEQUENCE CHARACTERISTICS:
        (A) LENGTH: 12 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO: 10:

TAGATTTACA AA                                      12

(2) INFORMATION FOR SEQ ID NO: 11:

(i) SEQUENCE CHARACTERISTICS:
        (A) LENGTH: 31 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 11:

GGGGCTCGAG TTAATACGAC TCACTATAGG G                    31

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 12:

CGTTGTAAAA CGACGGCCAG                             20

(2) INFORMATION FOR SEQ ID NO: 13:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 13:

CCGCATGCGA TCCGGCTGCT AACAAAGCC                      29

(2) INFORMATION FOR SEQ ID NO: 14:

(i) SEQUENCE CHARACTERISTICS:

(A) LENGTH: 31 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 14:

GGATATCAGA TCTCGATCCG GATATAGTTC C                                    31

(2) INFORMATION FOR SEQ ID NO: 15:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 15:

GGGCTCGAGT TAATTCGACT CACTATACGG                                      30

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 16:

CGTTGTAAAA CGACGGCCAG                                                 20

(2) INFORMATION FOR SEQ ID NO: 17:

(i) SEQUENCE CHARACTERISTICS:
        (A) LENGTH: 31 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 17:

GGGGCTCGAG TTAATACGAC TCACTATAGG G                                    31

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 18:

CGTTGTAAAA CGACGGCCAG                                                 20

(2) INFORMATION FOR SEQ ID NO: 19:

(i) SEQUENCE CHARACTERISTICS:
        (A) LENGTH: 29 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 19:

| CCGCATGCGA TCCGGCTGCT AACAAAGCC | 29 |

(2) INFORMATION FOR SEQ ID NO: 20:

(i) SEQUENCE CHARACTERISTICS:
        (A) LENGTH: 31 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO: 20:

| GGATATCAGA TCTCGATCCG GATATAGTTC C | 31 |

(2) INFORMATION FOR SEQ ID NO: 21:

(i) SEQUENCE CHARACTERISTICS:
        (A) LENGTH: 1921 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iii) ANTI-SENSE: NO (vi) ORIGINAL SOURCE:

(xi) SEQUENCE DESCRIPTION: SEQ ID NO: 21:

| ATTCTGTTCT TGGTTTACTT AATCTTCTTT CTAGTTAAGT ATATTCTTGT TGCTCATCAC | 60 |
| CAAAGCTTGT GATGGAGGCT CTCTTCTTGA GTTCTTCTTC TTCCTCCATT GTAGGGTCAA | 120 |
| ACAAGCTTAC TAGGTTACAC AACCATTGTG TCTGGTCTAC AGTGATTAGA GATAAGAAAA | 180 |
| GGTTCGGTCC CACTTGGTGC CGTGTAGGTG GTGGTGGTGA TGGTGGGAGA AACAGTAACG | 240 |
| CAGAGAGTCC TATTCGGGTT TCTTCGCTTT TGAAAGACAG AGGTCAGGTA CTGATTAGGG | 300 |
| AACAGAGTTC GCCGGCTATG GATGCTGAGA CATTGGTTCT GTCTCCAAAC GGGAATGGGA | 360 |
| GAACCATTGA GATCAATGGA GTAAAGACTT TGATGCCTTT TAGTGGCGCT TCTATGGTGG | 420 |
| GGATGAAAGA AGGACTTGGC ATAATCAGTT TCCTCCAAGG GAAGAAGTTT CTAATCACTG | 480 |
| GCTCGACCGG TTTCTTAGCT AAAGTACTGA TTGAGAAAGT CTTGAGAATG GCTCCTGATG | 540 |
| TCAGCAAGAT ATATCTCTTG ATTAAAGCCA AAAGCAAAGA AGCTGCGATC GAGCGGCTAA | 600 |
| GAACGAGGTG TTAGATGCAG AGCTTTTTAA TACTCTAAAA GAGACTCATG GAGCATCTTA | 660 |
| CATGTCTTTC ATGTTAACTA AACTCATCCC TGTGACCGGA ACATTTGCG ATTCAAACAT | 720 |
| TGGGTTGCAA GCAGATTCAG CTGAAGAGAT TGCGAAAGAA GTTGATGTTA TAATCAATTC | 780 |
| TGCTGCTAAT ACAACCTTCA ATGAAAGATA CGATGTTGCT CTGGACATCA ACACAAGAGG | 840 |
| GCCCGGTAAT CTCATGGGAT TCGCCAAGAA GTGCAAGAAA CTCAAACTGT TCTTGCAAGT | 900 |
| ATCCACAGCT TATGTGAATG GACAAAGACA AGGAAGGATC ATGGAGAAGC CATTTTCTAT | 960 |
| GGGAGATTGT ATAGCAACAG AGAACTTCCT CGAAGGAAAC AGAAAAGCAT TAGATGTTGA | 1020 |
| TAGAGAGATG AAGTTAGCTC TTGAAGCTGC TAGAAAAGGG ACTCAAAATC AAGATGAGGC | 1080 |
| ACAGAAGATG AAGGATCTCG GTCTAGAGCG GGCAAGATCA TATGGATGGC AAGACACTTA | 1140 |

-continued

```
TGTTTTCACC AAAGCAATGG GTGAGATGAT GATCAATAGC ACTCGAGGAG ACGTACCTGT    1200

TGTTATTATA AGGCCTAGCG TCATCGAAAG CACTTACAAA GATCCTTTCC CTGGATGGAT    1260

GGAAGGAAAC AGGATGATGG ATCCTATAGT TTTATGTTAC GGGAAGGGGC AACTCACGGG    1320

GTTTTTGGTT GATCCAAAAG GAGTTCTTGA TGTAGTTCCT GCTGATATGG TTGTTAATGC    1380

AACGTTAGCT GCTATAGCAA AGCATGGAAT GGCAATGTCA GATCCGGAAC CTGAAATAAA    1440

CGTGTATCAG ATCGCTTCTT CGGCGATAAA CCCGCTGGTT TTCGAAGACT AGCGGAGCT     1500

TCTTTATAAC CACTACAAAA CATCCCCATG CATGGACTCT AAAGGTGATC CTATTATGGT    1560

GCGTTTGATG AAACTTTTCA ATTCCGTTGA TGATTTCTCG GATCATTTGT GGAGAGATGC    1620

TCAAGAACGG AGTGGGTTGA TGAGTGGTAT GAGTTCAGCG GATAGTAAGA TGATGCAGAA    1680

GCTAAAGTTT ATATGCAAGA AATCTGTTGA ACAAGCCAAA CACCTTGCTA CTATTTATGA    1740

GCCATACACT TTCTATGGTG GAAGATTTGA TAACAGCAAT ACACAGAGAT TAATGGAGAA    1800

TATGTCAGAG GACGAGAAGA GAGAATTTGG ATTTGATGTT GGAAGCATTA ACTGGACGGA    1860

CTACATTACA AACGTTCACA TTCCCGGTTT AAGAAGGCAT GTCTTGAAAG GAAGAGCTTT    1920

A                                                                    1921
```

(2) INFORMATION FOR SEQ ID NO: 22:

(i) SEQUENCE CHARACTERISTICS:
        (A) LENGTH: 1920 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iii) ANTI-SENSE: NO (vi) ORIGINAL SOURCE:

(xi) SEQUENCE DESCRIPTION: SEQ ID NO: 22:

```
AATGGAATGG ACAGTTTACT GTCTTAGTCT AAAAATGAAC CTTTCTCTAT TTCTTATTTC      60

TTAGTTTGTG ATGGAAGCTC TCTTCTTGAG TTCTTCTTCC TCCTCCATTG CTGCTTCAAT     120

CAAGCTTTCA AGATTACACG ACCGTCGTGA CTGGTGCACT TTGTTAAGGG ACAAGAAAAG     180

GGTAGGACCC ACCTGGTGCC GCGTAGGTGG TGGTGGCGGT GATGGGAGAA ACATCAAACC     240

AGAGAGGCCT ATTAGGGTCT CATCGCTTTT GAAAGACAGA GGTCAAGTAT TGATTAGGGA     300

ACAGAGTTCG CCTGCTATGG ACGCTGAGAC ATTGGTTCTG TCACCTAATG TGAATGGTAC     360

AGCCATTGAG ATGAATGGAG TGAAAACTCT GATGCCTTCA ATGGTGCTGA TATGGTGGGG     420

ATCAAACAAG GACTTGGCAT CGTTAGTTAT CTACAAGGGA AGACGTTTCT AATCACTGGC     480

TCCACTGGCT TCTTAGCTAA AGTACTGATT GAGAAGGTCT TGAGAATGGC TCCTGATGTT     540

GGGAAAATAT ATCTCTTGAT TAAAGCTAAA AACAAAGAAG CAGCGATCCA GCGGTTAAAG     600

AACGAGGTGT TAGATGCAGA GCTTTTTAAA AATCTAAGAG AGACTCATGG AGCATCTTTC     660

ATGTCTTTCA TGTTAGACAA GCTTGTCCCT GTGACAGGAA ACATTTGCGA TTCAAACATT     720

GGGTTGCAAA CAGATTCAGC AGAGGAGATT GCAAAGAAG TTGATGTGAT TATCAACTCA      780

GCTGCCAATA CAACCTTCAA TGAAAGATAT GATGTTGCTT TGGACATAAA CACACGAGGG     840

CCTGGTAATC TCATGGGATT CGCCAAGAAG TGCAAGAAAC TCAAGCTTTT CTTGCAAGTA     900

TCTACAGCTT ATGTGAACGG ACAAAGACAA GGAAGGATCA TGGAGAAGCC CTTCTCGATG     960
```

```
GGAGATTGTA TAGCTACAGA GAACTTCATG GAAGGTAACA GGAAAGCATT AGATATCGAT    1020

AAAGAGATGA AGCTAGCTCT TGATGCTGCA AGAAAAGGGA CTCAAGATCA AGATGAGGCG    1080

CAGAAGATGA AGGATCTCGG TCTAGAGAGG GCAAGATCAT ATGGATGGCA AGACACTTAT    1140

GTTTTCACCA AAGCAATGGG AGAAATGATG ATCAATAGCA CTAGAGGGGA CGTACCTGTG    1200

GTTATTATAA GGCCTAGCGT CATCGAAAGC ACTTACAAAG ACCCTTTCCC TGGATGGATG    1260

GAAGGAAACA GGATGATGGA TCCTATAGTG CTGTGTTATG GAAAAGGACA GCTCACAGGG    1320

TTCTTGGTTG ATCCAAAAGG AGTTCTTGAT GTGGTTCCGG CTGATATGGT CGTTAATGCG    1380

ACATTAGCTG CTATAGCAAA GCATGGAATG GCTAAGGCAG ATACAGAACC TGAGATAAAC    1440

GTGTATCAGA TCGCTTCTTC AGCGATAAAT CCTCTTGTTT TCGAGGACTT AGCTGAGCTT    1500

CTTTATAACC ATTACAAATC TACCCCGTGC ATGGACTCGA AAGGTGTTCC TATTAGGGTG    1560

CCTTTGATGA AGCTTTTCGA CTCCGTTGAT GATTTCTCGG ATCATTTGTG GAGAGATGCT    1620

CAAGAACGGA GTGGATTAAT GAATGGTATG GACTCATCGG ATAGTAAGAT ACTACAGAAG    1680

CTTAAATTCA TTTGCAAGAA ATCTATTGAG CAAGCCAAAC ACCTTGCCAC TATTTATGAG    1740

CCATACACTT TCTATGGTGG AAGATTTGAT AACAGCAATA CACATAGATT AATGGAGAAT    1800

ATGTCTGAAG AAGAGAAGCT TGAGTTTGGG TTTGATGTTG GAAGCATTAA CTGGAATGAC    1860

TACATTACAA ATGTTCACAT TCCCGGTTTA AGAAGACATG TTTTGAAAGG AAGGGCTTAG    1920
```

(2) INFORMATION FOR SEQ ID NO:23:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:23:

```
Trp Val Ala Ser Lys Gly Asn Leu Ala Asp
1               5                   10
```

(2) INFORMATION FOR SEQ ID NO:24:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:24:

```
Xaa Ile Ala Ser Leu Gly Asn Leu Ala Asp
1               5                   10
```

(2) INFORMATION FOR SEQ ID NO:25:

(i) SEQUENCE CHARACTERISTICS:
        (A) LENGTH: 4 amino acids
        (B) TYPE: amino acid
        (C) STRANDEDNESS: single (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:25:

Thr Trp Arg Glu
1

(2) INFORMATION FOR SEQ ID NO:26:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:26:

Thr Xaa Arg Glu
1

(2) INFORMATION FOR SEQ ID NO:27:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:27:

Ala Gln Val Ile Asn
1               5

(2) INFORMATION FOR SEQ ID NO:28:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:28:

Ala Gln Val Xaa Asn
1               5

(2) INFORMATION FOR SEQ ID NO:29:

(i) SEQUENCE CHARACTERISTICS:
        (A) LENGTH: 4 amino acids
        (B) TYPE: amino acid

```
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:29:

Leu Ile Trp Lys
1

(2) INFORMATION FOR SEQ ID NO:30:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:30:

Xaa Leu Trp Lys
```